United States Patent [19]
Beachy et al.

[11] Patent Number: 5,898,097
[45] Date of Patent: Apr. 27, 1999

[54] RESISTANCE TO VIRUS INFECTION USING MODIFIED VIRAL MOVEMENT PROTEIN

[75] Inventors: Roger N. Beachy, La Jolla, Calif.; Moshe Lapidot, Jerusalem; Ron Gafny, Tel-Aviv, both of Israel

[73] Assignee: Calgene LLC, Davis, Calif.

[21] Appl. No.: 08/231,209

[22] Filed: Apr. 19, 1994

[51] Int. Cl.⁶ .............................. A01H 5/00; C12N 15/82; C12N 15/33

[52] U.S. Cl. ........................ 800/279; 435/69.1; 435/440; 435/468; 536/23.72

[58] Field of Search ........................... 800/205, DIG. 43; 435/172.3, 69.1, 240.4, 172.1; 536/23.72

[56] References Cited

PUBLICATIONS

Abel, Patrica Powell, Richard S. Nelson, Barun De, Nancy Hoffman, Stephen G. Rogers, Robert T. Fraley, and Roger N. Beachy, Delay of Disease Development in Transgenic Plants That Express the Tobacco Mosaic Virus Coat Protein Gene, Science, 232:738–743 (1986).
Deom, Carl M., Melvin J. Oliver, and Roger N. Beachy, The 30–Kilodalton Gene Product of Tobacco Mosaic Virus Potentiates Virus Movement, Science, 237:389–393, (1987).
Hull, Roger, The Movement of Viruses in Plants, Annu. Rev. Phytopathol., 27:213–240, (1989).
Dawson, William O., Relationship of Tobacco Mosaic Virus Gene Expression to Movement Within the Plant, Viral Genes and Plant Pathogenesis, pp. 39–57, (1990).
Citovaky, Vitaly, David Knorr, Gadi Schuster, and Patricia Zambryski, The P30 Movement Protein of Tobacco Mosaic Virus is a Single–Strand Nucleic Acid Binding Protein, Cell, 60:637–647, (1990).
Deom, Carl M., Karel R. Schubert, Shmuel Wolf, Curtis A. Holt, William J. Lucas, and Roger N. Beachy, Molecular Characterization and Biological function of the Movement Protein of tobacco Mosaic Virus in Transgenic Plants, Proc. Natl. Acad. Sci., 87:3284–3288, (1990).
Wolf, Shmuel, Carl M. Doem, Roger Beachy, and William J. Lucas, Plasmodesmatal Function is Probed Using Transgenic Tobacco Plants that Express a Virus Movement Protein, The Plant Cell, 3:593–604, (1991).
Berna, Anne, Ron Gafny, Shmuel Wolf, William J. Lucas, Curtis A. Holt and Roger N. Beachy, The TMV Movement Protein: Role of the C–Terminal 73 Amino Acids in Subcellular Localization and Function, Virology, 182:682–689 (1991).
Atkins, D., R. Hull, B. wells, K. Roberts, P. Moore and R.N. Beachy, The Tobacco Mosaic Virus 30K Movement Protein in Transgenic Tobacco Plants is Localized to Plasmodesmata, Journal of General Virology, 72:209–211, (1991).

Deom, Carl M., Shmuel Wolf, Curtis A. Holt, William J. Lucas, and Roger N. Beachy, Altered Function of the Tobacco Mosaic Virus Movement Protein in a Hypersensitive Host, Virology, 180:251–256, (1991).
Citovsky, Vitaly, Mei Lie Wong, Andrea L. Shaw, B. V. Venkataram Prasad, and Patricia Zambryski, Visualization and Characterization of Tobacco Mosaic Virus Movement Protein Binding to Single–Stranded Nucleic Acids, The Plant Cell, 4:397–411 (1992).
Deom, C. Michael, Moshe Lapidot, and Roger N. Beachy, Plant Virus Movement Proteins, Cell, 69:221–224, (1992).
Ding, Biao, James S. Haudenshield, Richard J. Hull, Shmuel Wolf, Roger N. Beachy, and William J. Lucas, Secondary Plasmodesmata are Specific Sites of Localization of the Tobacco Mosaic Virus Movement Protein in Transgenic Tobacco Plants, The Plant Cell, 4:915–928, (1992).
Gafny, Ron, Moshe Lapidot, Anne Berna, Curtis A. Holt, Carl M. Deom, and Roger N. Beachy, Effects of Terminal deletion Mutations on Function of the Movement Protein of Tobacco Mosaic Virus, Virology, 187:499–507, (1992).
Moore, Patricia J., Csilla A. Fenczik, C. M. Deom, and R. N. Beachy, Developmental Changes in Plasmodesmata in Transgenic Tobacco Expressing the Movement Protein of Tobacco Mosaic Virus, Protoplasma, 170:115–127, (1992).
Malyshenko, S. I., O. A. Kondakova, Ju. V. Nazarova, I. B. Kaplan, M. E. Taliansky, and J. G. Atabekov, Reduction of Tobacco Mosaic Virus Accumulation in Transgenic Plants Producing Non–Functional Viral Transport Proteins, Journal of General Virology, 74:1149–1156, (1993).
Lapidot, Moshe, Ron Gafny, Biao Ding, Shmuel Wolf, William J. Lucas, and Roger N. Beachy, A Dysfunctional Movement Protein of Tobacco Mosaic Virus that Partially Modifies the Plasmodesmata and Limits Virus Spread in Transgenic Plants, The Plant Journal, 4(6):959–970, (1993).
Beachy, R. N., Fitchen, N. Lapidot, R. Gafny, W. Lucas, A. Sturtevant, B. Ding, C. Malpica, Virus Resistance in Transgenic Plants Using Coat and Movement Protein Genes, abstract of oral presentation made at AgBiotech meeting held at Rutgers University, New Jersey, on Apr. 22, 1993. Printed abstracts made available at the meeting.
Abel et al (1986) Science 232:738–743 (IDS–AA).
Gafny et al (1992) Viral 187:499–507 (IDS–AN).
Deom et al (1992) Cell 69:221–224 (IDS–AL).
Hull et al (1989) Ann Rev. Phytopathol 27:213–240.

*Primary Examiner*—Elizabeth F. McElwain

[57] ABSTRACT

The present invention relates to the methods and nucleic acid compositions for the production of transgenic plants resistant to virus infection. In particular, it relates to transgenic plants comprising nucleotide sequences encoding dysfunctional viral movement protein (dMP) genes.

5 Claims, 12 Drawing Sheets

(a) Plant line 3A5-SX-11     (b) Plant line 3A6-NN-2

| MPΔ3-5 Accum. | Symptoms at 9DPI | MPΔ3-5 Accum. | No. of Lesions |
|---|---|---|---|
| ▬ | none | ▬ | 18 |
| ▬ | none |  | 52 |
| ▬ | none | ▬ | 11 |
| ▬ | none | ▬ | 20 |
| ▬ | none |  | 60 |
|  | severe | ▬ | 15 |
|  | severe | ▬ | 19 |
| ▬ | none |  | 83 |
|  | severe |  | 80 |
|  | severe | ▬ | 30 |
|  | severe | ▬ | 0 |
| ▬ | none |  | 100 |
|  | severe |  | 70 |

RESISTANCE TO VIRUS INFECTION USING MODIFIED VIRAL MOVEMENT PROTEIN

BACKGROUND OF THE INVENTION

The present invention relates to the methods and nucleic acid compositions for the production of transgenic plants resistant to virus infection. In particular, it relates to transgenic plants comprising nucleotide sequences encoding dysfunctional viral movement protein (dMP) genes.

Local as well as systemic viral infection requires virus movement. Opportunistic introduction of viral particles occurs where cell wall and plasma membrane integrity has been disrupted, as for example through mechanical damage caused by a biological vector such as an insect, nematode or fungus as-well-as abrasive forces such as the breaking of a leaf or branch. A progressive viral infection results if upon replication the viral progeny is capable of spreading into adjacent cells and then systemically throughout the plant. In certain instances infectious virus have been shown as capable of replication in the host cells but unable to move to adjacent healthy cells. When this occurs the infection is said to be subliminal and the plant appears resistant.

The cell-to-cell spread of virus is not a passive process but requires the expression of a virus encoded product called a movement protein (MP). The movement proteins of many viruses have been tentatively identified as reviewed by Hull, R., *Annu Rev Phytopathol* 27: 213–240 1989, and Maule, A. J., *Crit Tev Plant Sci* 9: 457–473 1991. The first virus-encoded movement protein (MP) identified was that of tobacco mosaic virus (TMV) (Deom et al., *Science*, 237 384–389 1987; and Meshi et al., *EMBO J* 6: 2557–2563 1987). Although dispensable for virus replication, the 30 kDa MP of TMV is essential for cell-to-cell spread of the infection (Deom et al., *Cell* 69: 221–224 1992). Furthermore, transgenic plants that express the TMV MP (MP(+) plants) can complement mutants of TMV that are movement deficient (Deom et al., supra 1987; Holt and Beachy, *Virology* 181: 109–117 1991). In both TMV-infected plants and MP(+) plants the MP co-purifies with an insoluble cellular component that contains cell walls (Deom et al., *Proc Natl Acad Sci* 87: 3284–3288, 1990), and was localized by immunogold labeling to the plasmodesmata, the cytoplasmic connections between adjacent plant cells. Specifically, the TMV MP is localized to the central cavity of secondary (also referred to as modified primary) plasmodesmata which are formed through fusion of, and addition of, new protoplasmic bridges to primary plasmodesmata (Ding et al., *Plant Cell*, 4: 915–928, 1992).

The mechanism(s) by which the MP potentiates virus movement from cell to cell is not fully understood. Wolf et al., *Science* 246: 377–379, 1989, demonstrated through dye coupling studies that the protein has a direct effect on the molecular size exclusion limit (SEL) of the plasmodesmata. Fluorescent dextrans with an average molecular mass of 9400 Da moved between cells of MP(+) transgenic plants, while the size exclusion limit of the MP(-) transgenic plants and non-transgenic plants was 700–800 Da. In a similar study a temperature-sensitive (ts) mutant of the MP was unable to modify the SEL of plasmodesmata or to facilitate virus movement at the non-permissive temperature (Wolf et al., *Plant Cell* 3: 593–604, 1991).

Deletion mutants of TMV MP have been made and expressed in transgenic plants. Berna et al., *Virology,* 182: 682–689, 1991, studied transgenic plants that expressed truncated MP lacking up to 73 C-terminal amino acids. The transformed plants were analyzed for MP subcellular localization and for complementation of the spread of a thermosensitive TMV mutant Ls1. Ls1 is incapable of cell-to-cell movement at the non-permissive (32° C.) temperature due to an inactivated MP. Deletion of the C-terminal 55 amino acids of MP had no effect on subcellular localization or complementation of Ls1. Deletion of an additional 19 aa (aa 195 to 213 aa) destroyed both cell localization and ability to complement Ls1.

Gafny, et al., *Virology* 187: 499–507 1992, studied a variety of infectious clones of TMV having N-terminal and C-terminal deletions in the MP gene. The effect of the deletion mutations on local and systemic movements of the infection was evaluated. Deletion of 9 to 33 C-terminal amino acids did not effect cell-to-cell movement as reflected by local lesion formation on *Nicotiana tabacum* cv. Xanthi NN plants. Deletion of 55 C-terminal amino acids resulted in impaired movement and deletion of 74 C-terminal amino acids resulted in a protein that could not support virus movement. In addition, MP deleted for N-terminal amino acids 3–5 could not support virus movement.

Although a number of mutations in the TMV MP are found to alter the ability of the protein to support virus spread, the effect such mutations have on the production of a MP capable of blocking the spread of virus infection was not determined. It is the determination that dysfunctional MP can lead to viral resistance in plants, the resultant dysfunctional MP and the virus resistant transgenic plants that are the subject of the present invention.

SUMMARY OF THE INVENTION

The present invention provides and claims methods for producing viral resistant transgenic plants that are transformed by a gene encoding a mutated viral movement protein. The mutation causes the protein to dysfunction as a virus movement protein but retain the ability to interact with the plant constituents in such a manner as to block the spread of infectious virus.

The invention further provides the mutation is at the N-terminus of the protein between amino acids 2 and 8 and preferably is a deletion of amino acids 3, 4 and 5.

The dysfunctional virus movement protein is derived from a Tobamovirus, preferably tobacco mosaic virus, and is capable of inhibiting the spread of viruses from a number of different groups or families including Ilar viruses which includes alfalfa mosaic virus, bromovirus, caulimorvirus, hordeivirus, luteovirus, tobamovirus, and tospovirus.

Plant species benefited by transformation with such a dysfunctional virus movement protein gene include, but are not restricted to tobacco, tomato, bean, potato, barley, wheat, cucumbers, melons and corn.

In general, the methods described herein are applicable to any virus movement protein. Where the spread of a viral plant disease is the result of a viral movement protein allowing for the intercellular and/or systemic movement of a particular virus, this invention makes it possible for the trained artisan to mutate and test the movement protein and identify a dysfunctional movement protein that will interfere with virus movement. In this regard, this invention further provides for mutated viral movement proteins that interfere with virus movement.

BRIEF DESCRIPTION OF THE DRAWINGS

FIG. 1 shows the correlation of disease resistance with accumulation of MPΔ3–5. (a) Xanthi nn plants were inoculated with TMV (0.25 μg/ml) and were observed for systemic disease symptoms 9 DPI. Under the conditions of these experiments symptoms were visualized on non-transgenic Xanthi nn plants by 4–5 DPI. (b) Xanthi NN plants were inoculated with TMV (1.0 µg/ml) and lesions were counted 48–72 h post-inoculation. Plants were assayed for accumulation (Accum.) of MPΔ3–5 by a slot-blot immunological assay as described in the examples. Thirteen plants from each line are presented; however, 45 plants from each line were tested in the experiment. The MPΔ3–5 gene segregated 3:1 in both lines.

FIG. 3 shows the time course of development of systemic disease symptoms in plants inoculated with TMV or TMGMV. Seedlings of the Xanthi nn transgenic plant line 3A5-SX-11 that express the MPΔ3–5 gene [3A5-11(+)], non-expressing transgenic plants [3A5-11(−)], and non-transgenic Xanthi nn plants (WT) were inoculated with: (a) 0.25 ug/ml TMV; (b) 1.0 ug/ml TMV; (c) 1.3 ug/ml TMV-RNA; (D) 2.0 ug/ml TMGMV. A plant was determined to be systemically infected when it exhibited mosaic symptoms, or strong vein clearing, in more than one leaf.

FIG. 4 shows transgenic plants that accumulate the MPΔ3–5 develop lower numbers, and smaller necrotic local lesions upon inoculation with TMV and TMGMV. Non-transgenic Xanthi NN plants and MPΔ3–5(+) plants (line 3A5-NN-7B) were inoculated with (a) TMV (1.0 ug/ml) or (b) TMGMV (2.0 ug/ml). Lesion sizes were measured at daily intervals. Between 60 and 120 lesions were measured at each time point for the Xanthi NN plants, and 150–250 for the 3A5(+) plants. Bars represent standard error. HPI, hours post-inoculation.

FIG. 5 shows the number of leaves with symptoms of tobamovirus Ob infection as a function of time. One Leaf on each plant was inoculated with [the tobamovirus] Ob with an IP that resulted in 14 lesions per leaf on *C. amaranticolor*. NN (MP−)=○ 2005 (MP+)=□, 3A5-NN-7B (dMP)=Δ, 3A6-NN-2 (dMP)=◇. *=At this day the symptoms for 3A5-NN-7B and 3A6-NN-2 as compared to NN differ significantly at the 5% level.

FIG. 6 shows the number of leaves showing symptoms of TRV as a function of time. One leaf on each plant was inoculated with TRV with an IP that resulted in 260 lesions per leaf on *C. amaranticolor.* NN (MP−)=○, 2005 (MP+)=□, 3A5-NN-7B (dMP)=Δ, 3A6-NN-2 (dMP)=◇. *=At this day the symptoms for 3A5-NN-7B and 3A6-NN-2 as compared to NN differ significantly at the 5% level.

FIG. 7 shows the number of leaves showing symptoms of AlMV as a function of time. One leaf on each plant was inoculated with AlMV with an IP that resulted in 25 lesions per leaf on *C. amaranticolor.* (a) NN (MP−)=○, 2005 (MP+)=□, 3A5-NN-7B (MPΔ3–5)=Δ, 3A6-NN-2 (MPΔ3–5)=◇; (b) 3A7-SX-8 (MP−)=●, 274 (MP+)=■, 3A5-SX-11 (MPΔ3–5)=▲. *=At this day the symptoms for 3AS-NN-7B and 3A6-NN-2 as compared to NN or 3A5-SX-11 as compared to 3A7-SX-8 differ significantly at the 5% level.

Definitions

"Amino terminus" refers to that end of the protein which has the free primary amine.

"Intercellular movement" refers to the passage of viral nucleoprotein and/or nucleic acid from cell to cell. Typically this passage occurs through plasmodesmata which are modified by viral movement proteins to permit viral transfers.

"Movement protein" are viral proteins which bind to the plant cell walls and permit or facilitate travel of infectious viral components from cell to cell through the plasmodesmata. They are sometimes referred to as wild type (wt) movement proteins or MP when the text attempts to differentiate functional movement proteins from mutated movement proteins.

"Mutated movement proteins" are movement proteins that have been modified to inhibit the travel or passage of viral components through the plasmodesmata. They are also referred to as dysfunctional movement proteins or dMP. **

"Bind the cell walls" refers to the interaction that is predominantly more with the cell wall, plasma membrane or plasamadesmata of a plant relative to the other cellular components. Typically, with any commonly practiced method of plant cell fractionation that results in a cell wall enriched fraction, a larger percentage of the cellularly expressed mutated movement protein will be associated with the cell wall fraction. The cell wall fraction will contain fragments of plasma membrane and plasmodesmata. The mutated movement protein can also be defined as having subcellular localization to the cell wall, plasma membrane or plasmodesmata or accumulated at the cell wall, plasma membrane or plasmodesmata.

"Viral resistant plant" refers to a plant that resists the cell-to-cell spread of virus particles. The cell-to-cell spread of virus infection can be systemic where by symptoms of infection develop at a site on the plant distant from the initial inoculation site, or virus spread may be restricted to an area of necrosis where by symptoms of infection are exemplified by local lesions. In addition, the cell-to-cell spread of virus can remain localized near the inoculation site without the development of lesions. In an assay, resistance that is more than 40% of the resistance of the control in either by symptom intensity or viral titer measured by immunoassay, direct examination under an electron microscope, qualitative assay such as a bioassay on a reporter plant (e.g. *C. amaranticolor*) or by other quantification means.

DETAILED DESCRIPTION

This invention provides transgenic plants resistant to viral infection. Virus resistance results from the transgenic expression of a gene encoding a dysfunctional virus movement protein. The dysfunctional movement protein confers resistance to the plant by competing with and blocking the wild type movement protein of the otherwise infecting virus. The invention describes methods for mutating viral movement protein genes, transforming plants with the mutated gene and analyzing the transgenic plants for resistance to virus infection and spread. In addition, transient assays are provided that allow for the rapid selection of promising dysfunctional movement proteins that can be tested further in transgenic plants.

The mutation of wild type movement proteins to produce novel mutant movement proteins is done by conventional means. Movement proteins are identified genetically by analyzing the viral genome for gene sequences, which when altered, restrict the ability of the virus to spread locally or systemically, but do not alter the ability of the virus to replicate or assemble. A number of movement proteins have been described in the literature. They include those of tobacco mosaic tobamovirus (Deom et al, 1987, supra); cowpea mosaic comovirus (van Lent, Wellink, and van Kammen, *J Gen Virol* 71: 219, 1989); brome mosaic bromovirus (Sacher and Ahlquist, *J Virology,* 63: 4545, 1989); red clover mottle virus (Shanks et al, *Virology,* 173: 400, 1989).

Figure 2:
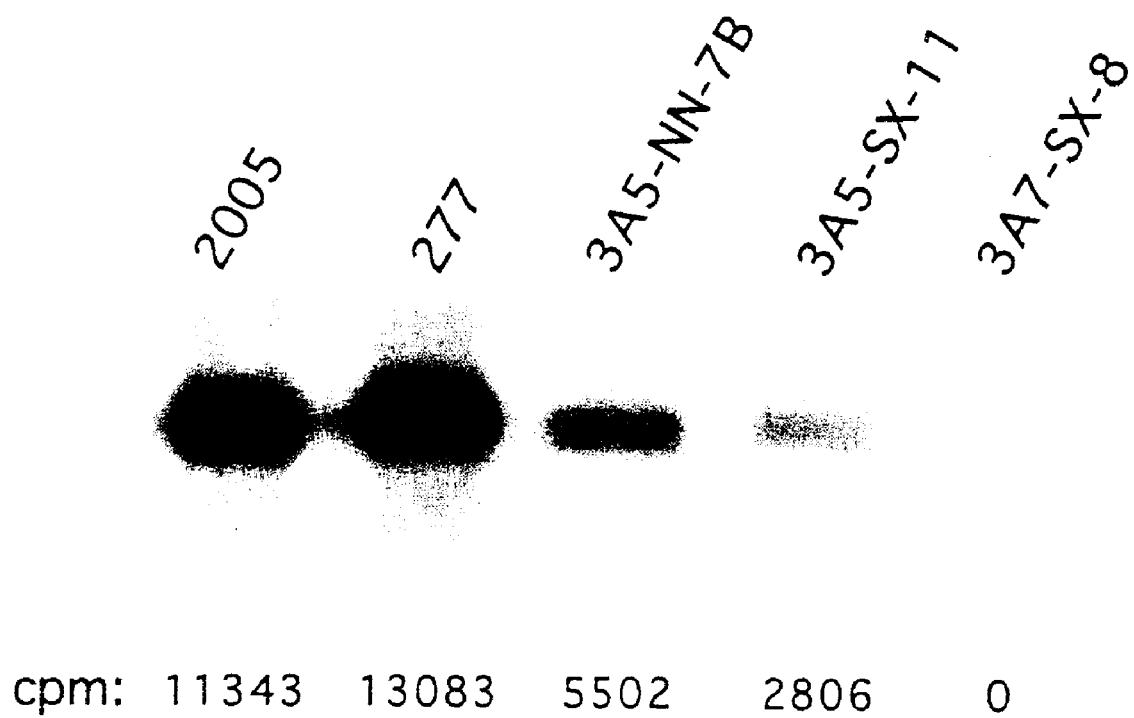
FIG. 2 shows the accumulation of MP and MPΔ3–5 in transgenic plants. Total cellular proteins were extracted from leaf tissues as described in the examples. Leaves from three plants of each genotype were pooled for analysis. The proteins were separated on a 12.5% polyacrylamide gel (50 µg protein per lane), transferred to nitrocellulose and reacted with anti-MP antibodies followed by $^{125}$I-labeled secondary antibody. The MP and MPΔ3–5 were excised from the membrane and quantitated in a γ counter; c.p.m. are given below each lane. 2005 and 277 are transgenic plant lines that express the MP of TMV (Deom et al., supra 1987); 3A5-NN-7B and 3A5-SX-11 are transgenic plant lines which express the MPΔ3–5; 3A7-SX-8 is a transgenic line that does not express the MPΔ3–5 gene.

The exemplified mutant movement protein disclosed herein is a 3–5 amino acid deletion (MPΔ3–5). Other mutations are possible based upon the teachings herein. It is not possible to describe all the possible mutations from each viral movement protein that will interfere with viral passage from cell to cell. One of skill could readily provide numerous conserved substitutions in the exemplified mutated movement protein. For example the neutral amino acids could be substituted with glycine or alanine and aspartic acid residues could be changed to glutamic acid. There is no limit to the number of conserved substitutions or additions or deletions that could be tested and a substantial number of such modified proteins would be the equivalent of the mutated (dysfunctional) TMV movement protein described herein. Amino terminal deletions are preferred however amino acid substitution would also function to provide suitable mutations.

There are various means for producing mutations. Routine recombinant methods are the most convenient means. Single site mutations can be introduced by a variety of routine methods such as the M13 system. Most preferably, fragments of synthetic nucleic acid containing the desired mutations can be introduced by a combination of endonuclease cleavage and ligation. Controlled nuclease activity can be used to delete portions of the wild type gene (Maniatis et al., Molecular Cloning: A laboratory manual; Cold Spring Harbor Laboratory, Press, Cold Spring Harbor, N.Y.). Alternatively, point mutations and small deletions are made by directed mutagenesis reactions (Nakamaye and Eckstein, *Nucleic Acids Research,* 14: 9679–9698, 1986).

The mutations must retain the ability of the movement protein to bind to the plasma membrane and the plant cell wall while producing the desired inhibitory effect of blocking the wild type movement protein from permitting passage of infectious viral components from cell to cell. In addition, such mutations must not disrupt the intracellular stability of the protein and make it susceptible to the degradative pathways of the plant cell. It is known that the TMV movement protein is sensitive to substantial mutations. If you delete amino acids 3-8 of the protein, the structure of the molecule is sufficiently altered that the ability of the protein to bind cell walls is effected and resulting protein while dysfunctional and mutated may not be useful as a viral inhibitory agent.

For this reason, once the mutated proteins are produced each protein must be tested in accordance with the methods and assays produced herein. Following the teachings presented herein a significant number of mutated movement protein can be obtained that are suitable for inhibiting the cell to cell spread of viral infection. Suitable mutations for use in this invention are readily identified by routine titration experiments. For example, Table 1 lists a number of three amino acid deletions (TAD) of the movement protein that were made in TMV. The infectious potential of the mutated virus was studied on transgenic (MP+) and wild type systemic and local lesion host, Xanthi NN and Xanthi nn, respectively, of *Nicotiana tabacum.* Proteins 1–4 and 9 are examples fitting the criteria for conferring virus resistance.

Subcellular localization was determined with a transgenic plant expressing a functional movement protein deleted of 26 amino acids at the C-terminus, (Berna et al., 1991, supra). The viral expressed mutated movement protein was detected in cell wall enriched fractions using SDS-PAGE electrophoresis and western immunoblot analysis, the viral movement protein discerned from the transgenically expressed movement protein on the basis of size. Those virus that were infectious only after complementation by the MP of the transgenic plant and showed subcellular localization to the cell wall were considered to have dMP that would provide resistance when transformed and tested in transgenic plants. This experimental strategy and modifications thereof that are readily apparent to those of skill can be employed to identify other mutations of any plant viral movement protein for use in this invention.

In this regard, this invention encompasses virus that encode mutated movement proteins where the virus are infectious after complementation by a functional movement protein, and preferably are found to express a mutated movement protein that binds preferentially to the cell wall. The complementing functional movement protein does not necessarily need to be wild type movement protein but can be any movement protein altered by any means either genetically or chemically while retaining native function.

TABLE 1

Function of three AA deletions (TAD) of the MP in tobacco mosaic virus infections.

| | | | Genotype of the host:* | | | | |
|---|---|---|---|---|---|---|---|
| | | Position of | Xanthi NN | | Xanthi nn | | Subcellular |
| TAD | Deleted AA | Deleted AA | MP+ | WT | MP+ | WT | localization |
| 1 | Val, Asn, Ile | 9–11 | + | − | + | − | CW |
| 2 | Lys, Met, Glu | 19–21 | + | − | + | − | CW |
| 3 | Thr, Pro, Val | 29–31 | + | − | + | − | CW |
| 4 | Val, Asp, Lys | 39–41 | + | − | + | − | CW |
| 5 | Ser, Leu, Ser | 49–51 | + | − | + | − | |
| 6 | Val, Lys, Leu | 59–61 | + | − | + | − | |
| 7 | Leu, Ala, Glu | 69–71 | + | − | + | − | |
| 8 | Asn, Leu, Pro | 79–81 | + | − | + | − | |

TABLE 1-continued

Function of three AA deletions (TAD) of the MP in tobacco mosaic virus infections.

| | | | Genotype of the host:* | | | |
| | | Position of | Xanthi NN | | Xanthi nn | | Subcellular |
| TAD | Deleted AA | Deleted AA | MP+ | WT | MP+ | WT | localization |
|---|---|---|---|---|---|---|---|
| 9 | Val, Ser, Val | 88–90 | + | – | + | – | CW |
| 10 | Arg, Ala, Asp | 99–101 | + | – | + | – | |
| 11 | Tyr, Thr, Ala | 109–111 | + | – | + | – | |
| 12 | Phe, Lys, Val | 119–121 | + | – | + | – | |
| 13 | Thr, Gln, Asp | 129–131 | + | – | + | – | |
| 14 | Val, Leu, Val | 139–141 | + | – | + | – | |
| 15 | Ser, Ala, Gly | 149–151 | + | – | | | |
| 16 | Phe, Val, Ser | 159–161 | + | – | | | |
| 17 | Asn, Ile, Lys | 169–171 | | | | | |
| 18 | Thr, Asn, Val | 179–181 | | | | | |
| 19 | Leu, Thr, Glu | 189–191 | + | + | + | + | |
| 20 | Glu, Asp, Val | 199–201 | | | | | |
| 21 | Lys, Phe, Arg | 209–211 | + | – | + | – | |
| 22 | Asp, Val, Arg | 219–221 | + | + | | | |
| 23 | Asp, Arg, Ser | 229–231 | + | – | + | – | |
| 24 | Asn, Val, Lys | 239–241 | + | + | + | + | ND |
| 25 | Lys, Lys, Asn | 249–251 | + | + | + | (m)+ | ND |
| 26 | Glu, Ala, Thr | 259–261 | + | + | – | – | ND |

* '+' = infection
'–' = no infection
TAD = Three amino acid deletion;
AA = Amino acids;
WT = wild type.
Xanthi NN expressing the MP gene (MP+) = line 2005.
Xanthi expressing the MP gene (MP+) = line 277.
m = mild
ND = Not done.

In addition, there are described herein transient assays that detect competition between wild type and dysfunctional movement protein that are simultaneously expressed in a single plant either from a single viron or infectious transcript containing a simultaneous expression cassette or as separate co-inoculated infectious clones. If the mutated movement protein functions to inhibit the movement of virus, it can be presumed that the mutated movement protein is a part of this invention.

A. Methods of Virus Propagation

In general, the invention is applicable to any species of virus that requires a movement protein to spread infection either systemically or locally. Plant virology is a well developed area of technology. There are routine methods for propagating plant viruses as described in (Matthews, ed. "Diagnosis of Plant Virus Diseases," CRC Press, Boca Raton, Fla., pp 130–152, 1993). Virus identification is done by inoculation to diagnostic host plants and by reactions to virus specific antibodies, methods commonly used in the field of plant virology. Many commonly identified plant virus are available from the American Type Culture Collection.

B. Methods of Genetic Analysis and Manipulation

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual*, Cold Spring Harbor Laboratory, Cold Spring Harbor, N.Y., 1989.

The identification and isolation of a viral movement protein gene from a particular virus may be accomplished by a number of techniques. As summarized in Table 1 from Hull, supra, 1989, there is evidence that a large number of virus groups including, alfalfa mosaic, bromovirus, caulimovirus, comovirus, cucumovirus, dianthovirus, geminivirus, hordeivirus, ilarvirus, nepovirus, potexvirus, potyvirus, tobamovirus, tobravirus and tospovirus have viral-coded cell-to-cell movement proteins. Such evidence is the result of experiments involving subliminal infection, complementation, mutation, cytology and sequence homology.

In general, using techniques designed to clone virus genomes (see, e.g., Sambrook et al., 1989, supra) one can obtain a cDNA clone of a particular virus, and through sequence analysis define putative open reading frames which can be subcloned for further studies. Antibodies raised to oligopeptides of the predicted protein sequences can then be used to analyze for protein expression during the virus infection cycle, to determine protein interaction with different cellular components using cell fractionation studies, and to directly observe and localize the movement protein through electron microscopy and immunogold labeling of thin sections of infected plant tissues. Detailed descriptions of such techniques as well as further reference to experimental materials and methods can be found in Hull, supra, 1989, incorporated herein by reference.

C. Methods of Transferring Genes to Plants a. Agrobacterium-Mediated Transfer

This approach provides a routine and efficient system to transfer dMP to a variety of plant species. Agrobacterium tumefaciens-meditated transformation techniques are the most commonly used techniques for transferring genes into plants.

All species which are a natural plant host for Agrobacterium are transformable in vitro. Most dicotyledonous species can be transformed by Agrobacterium. Monocotyledonous plants, and in particular, cereals, are not natural hosts to Agrobacterium. There is growing evidence now that certain monocots can be transformed by Agrobacterium. Using novel experimental approaches cereal species such as rye (de la Pena et al., *Nature* 325: 274–276, 1987), corn (Rhodes et al., *Science* 240: 204–207, 1988), and rice (Shimamoto et al., *Nature* 338: 274–276, 1989) may now be transformed.

The transfer of genetic material is brought about by a segment of the Ti plasmid carried by A. tumefaciens known as T-DNA. When the T-DNA is transferred to the nuclear genome of a susceptible plant transformation occurs. As it naturally occurs on the Ti plasmid, the T-DNA is flanked by 25 bp direct repeats and contains genes that encode enzymes involved in the synthesis of auxin and cytokinin, the over production of which leads to uncontrolled cell proliferation and resultant transformation. By disarming the auxin and cytokinin genes and inserting a gene of interest, the T-DNA becomes a vehicle by which genetic sequences can be stably transferred into plants.

Regions of the T-DNA have been cloned in *E. coli* and used to construct plasmids that carry markers for selection and propagation in both bacteria and transgenic plants and are capable of homologous recombination with disarmed resident Ti plasmids in A. tumefaciens. Such plasmids are designed to carry transcriptional promoters that will drive the expression of a selected gene in the transformed plant. For example, pMON316 is a plasmid that contains drug resistance markers for selection and cloning in *E. coli*, i.e., spectinomycin/streptomycin (Spc/Str); a marker for selection in transformed plants, i.e., neomycin phosphotansferase type II (Npt II), and a nopaline synthase gene (Nop Syn); a region of homology for recombination with a resident Ti plasmid in A. tumefaciens; and the CaMV 35S promoter and NOS 3' untranslated region separated with a polylinker into which a gene of interest can be inserted, (Sanders et al., *Nucl Acids Res*, 160: 363–371, 1987).

Detailed procedures for Agrobacterium-mediated transformation of different plant species have been described by Horsch, et al., *Science*, 227: 1229–1231, 1985; Ulian, et al., *In Vitro Cellul Dev Biol* 24: 951–954, 1988; McGranahan, et al., *Bio/Technology* 6: 800–804, 1988; Fillati, et al., *Populus, Mol Gen Genet* 206: 192–199, 1987; James, et al., in *Genetic Engineering of Crop Plants*, 49th Nottingham Easter School (G. Lycett and D. Grierson, eds.), pp. 239–248, Sutton Bonington, University of Nottingham, Butterworths, UK, 1990.

b. Electroporation

In this technique, protoplasts are made by removing the plant cell wall using hydrolytic enzymes in an osmotically balanced solution. By subjecting the protoplasts, while in a solution of DNA, to a sharp discharge of electricity, pores open on the plasmalemma of the protoplast through which the DNA can enter. A small fraction of the DNA integrates into the plant's chromosomes and result in protoplasts that stably express the gene through which transformatin is confirmed. Once stable transformation is established, the protoplasts are treated to promote cell wall regeneration and further development to a whole plant which will then yield transgenic plants. General techniques for making and electroporating protoplasts from woody plants are published by Revilla et al., *Plant Sci* 50: 133–137, 1987.

c. Biolistic Method

This technique involves high velocity penetration of the plant cell wall with dense particles of gold or tungsten coated with DNA. Detailed descriptions of this technique is published by Klein et al., *Nature* 327: 70–73, 1987.

D. Methods of Transgenic Plant Selection and Propagation

After transformation, transformed plant cells or plants comprising the introduced DNA must be identified. A selectable marker, such as those discussed above is typically used. Transformed plant cells can be selected by growing the cells on growth medium containing the appropriate antibiotic. The presence of opines can also be used if the plants are transformed with Agrobacterium.

After selecting the transformed cells, one can confirm expression of the desired heterologous structural gene using a number of different techniques. Simple detection of mRNA encoded by the inserted DNA can be achieved by well known methods in the art, such as Northern blot hybridization. One can us immunoprecipitation or Western blot analysis if antibodies to the desired protein are available. The inserted sequence can be identified using the polymerase chain reaction (PCR) and Southern blot hybridization, as well. Detailed description of these techniques are found in Sambrook, 1989, supra.

Transformed plant cells (e.g., protoplasts) which are derived by any of the above transformation techniques can be cultured to regenerate a whole plant which possesses the transformed genotype and thus the desired viral resistant phenotype. Such regeneration techniques rely on manipulation of certain phytohormones in a tissue culture growth medium. Plant regeneration from cultured protoplasts is described in Evans et al., *Protoplasts Isolation and Culture, Handbook of Plant Cell Culture*, pp. 124–176, MacMillilan Publishing Company, New York, 1983; and Binding, *Regeneration of Plants, Plant Protoplasts*, pp. 21–73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467–486, 1987.

Accumulation of dMP in the leaves of transgenic plants indicates stable expression and possible resistance. As a preliminary analysis for the expression of dMP in transgenic plants rapid screening methods that identify plants that accumulate MP can be developed. For example, leaf tissue can be ground and soluble proteins extracted by standard means. The proteins can be absorbed to nitrocellulose and detection made using labeled antibodies specific for the protein of interest.

E. Methods for Testing Virus Resistance

To test for resistance to virus infection the transgenic plant is inoculated with a requisite virus and observed overtime on leaves the development of disease symptoms. For example, TMV resistance is typically tested on cultivars of *Nicotiana tabacum*. In particular, systemic spread of infection maybe evaulated using a systemic host such as cultivar Xanthi nn, and infection that is restricted to an area of necrosis maybe evaluated using a local lesion host such as cultivar Xanthi NN. Systemic hosts, i.e. *Nicotiana tabacum* cvs. Xanthi nn is a systemic host for TMV, and hosts in which infection is restricted to an area of necrosis, i.e. cvs. Xanthi NN, a "local lesion" host for TMV, can be used to test for virus resistance. With systemic hosts inoculum is applied to a select leaf, preferably a lower mature leaf, and development of disease symptoms is observed for over time on leaves distant from the inoculation site, such as the developing younger upper leaves. With a local lesion host, the number of necrotic local lesions are counted per inoculated leaf. Inoculation is done by disrupting the protective outer layers of plant tissue, as for example by rubbing leaves with carborundum, and applying the virus. In addition to using whole virus, the viral RNA can also act as the infectious agent.

The following examples are provided by way of illustration only and not by way of limitation. Those of skill will readily recognize a variety of noncritical parameters which could be changed or modified to yield essentially similar results.

EXAMPLES

Example 1

Preparation and Analysis of Transgenic Plants that Express Dysfunctional Viral Movement Proteins and are Resistant to the Spread of Virus Infection This example describes how to produce transgenic plants resistant to the spread of virus infection. *Nicotiana tabacum* cvs. Xanthi nn and Xanthi NN plants were transformed with a chimeric gene encoding a dysfunctional tobacco mosaic virus movement protein that lacks amino acids 3, 4 and 5 (MPΔ3–5). Tissue fractionation studies showed only a low level of MPΔ3–5 accumulated in the cell wall-enriched fraction compared with transgenic plants that accumulate wild-type MP. In addition, dye coupling studies showed that MPΔ3–5 enabled the movement between leaf mesophyll cells of a fluorescently labeled dextran of 3 kDa, while 9.4 Kda molecules failed to move. This is in contrast to transgenic plants expressing the wild-type MP gene where the 9.4 kDa probe did move from cell to cell. Viral resistance was studied by inoculating the seedings from self-fertilized transgenic plants with either; TMV, TMV-RNA, or the tobamoviruses TMGMV (tobacco green mosaic virus) or SHMV (sunnhemp mosaic virus), and observing the development of disease symptoms. In summary, in all instances disease development was inhibited in transgenic Xanthi NN and Xanthi nn plants expressing the MPΔ3–5 gene.

a) Genetic Manipulations and Preparation of Dysfunctional Viral Movement Protein DNA manipulations such as plasmid preparation, restriction, and ligation were essentially as described by Sambrook et al., 1989, supra. DNA sequencing was done as described by Tabor and Richardson, *Proc Natl Acad Sci USA* 84, 4767–4771, 1987. Transcription and translation reactions were performed using T7 RNA polymerase and wheat germ extract purchased from Promega Corporation, Madison, Wis., according to the manufacturer's instructions. RNA was extracted from plants as described by Logemann et al., *Anal. Biochem.* 163, 16–20, 1987.

Site-directed mutagenesis of the cloned cDNA encoding the TMV MP is described in Gafny, R., et al., 1992, supra. Briefly, N-terminal deletions as that found in the MPΔ3–5 gene were constructed using the in vitro mutagenesis system purchased from Amersham Corporation, Arlington Heights, Ill. The MP gene originated from plasmid pTM934 described by Oliver, M. J., et al., *Virology* 155, 277–283, 1986. The EcoR1-BamH1 fragment from PTM934 was cloned into the EcoR1-BamH1 sites of pBluescript KS+ purchased from Stratagene, La Jolla, Calif. Single stranded DNA was prepared and used as a template for site-directed mutagenesis. Synthetic oligonucleotides corresponding to 16–20 nucleotides from the 5' and the 3' boundaries of the deletion were used to mutate the MP gene. The amino-terminal first two amino acids of the MP were retained to preclude impairment in translation initiation.

The cloned cDNA encoding the MPΔ3–5 protein was ligated into the intermediate plasmid pMON316 described by Sanders, P. R., et al., 1987, supra, between the CaMV 35S promoter and the nopaline synthase 3' untranslated region. Agrobacterium tumefaciens-mediated gene transfer was done as describe by Horsch, R. B., et al., 1985, supra, was used to introduce the MPΔ3–5 gene into *N. tabacum* cvs. Xanthi nn and Xanthi NN as previously described by Deom, C. M., et al., 1990, supra.

b) Characterization of Transgenic Plants Expressing the Dysfunctional Viral Movement Protein Gene Two tobacco cultivars were used for transformation experiments with the MPΔ3–5 gene, *N. tabacum* cvs. Xanthi nn, a systemic host for TMV, and Xanthi NN, a host in which infection is restricted to an area of necrosis, i.e., a "local lesion" host. Eleven parental ($R_O$) Xanthi NN and 20 Xanthi nn plants were regenerated and taken to seed ($R_1$ seeds). Plants were grown in a growth room under artificial light (14 h light/10 h dark period) at 25–30° C.

Plants were analyzed for accumulation of MPΔ3–5 protein using the following procedure with the results shown in FIG. 1. Twenty milligrams of leaf tissue was ground in 100 μl of extraction buffer (75 mM Tris-Hcl, Ph 6.8, 6 M guanidine-Hcl), incubated in boiling water for 5 min, and the insoluble material was discarded following centrifugation for 5 min in a microcentrifuge. The soluble extract was applied to nitrocellulose with a slot-blot apparatus, reacted with anti-MP antibodies, Deom et al., 1987, supra, and then with $^{125}$I-labeled donkey anti-rabbit serum purchased from Amersham, supra. For experiments that required greater amounts of material, total cellular proteins were extracted by grinding 1 g of leaf tissue in 2 ml extraction buffer, incubated in boiling water for 5 min, and the insoluble material was discarded following centrifugation for 10 min at 10,000 g.

To determine if the MPΔ3–5 protein expressed by the transgenic plants were capable of inferring viral resistance, five plants from each line were inoculated with TMV and observed for delay or inhibition of local or systemic disease symptom development with the results shown in table 2.

Where inoculation is referred to here as well as throughout the examples, the leaves were mechanically inoculated using carborundum as an abrasive. The inoculum, i.e., TMV, TMV-RNA, TMGMV, or SHMV, was diluted to the appropriate concentration in inoculation buffer (20 Mm phosphate, Ph 7.2, 1 mM EDTA). After inoculation with 100 μl per leaf the leaves were rinsed with water and the plants were observed daily for disease symptoms.

Progeny of six of the 12 transgenic Xanthi NN plant lines and 16 of the 20 transgenic Xanthi nn plant lines, exhibited a degree of inhibition of viral spread based upon the criteria shown. Furthermore, it was found that reduction of spread of infection correlated with accumulation of MPΔ3–5 protein as shown in FIG. 1 and table 2.

R1 progeny of two transgenic tobacco lines, 3A5-NN-7B (Xanthi NN line) and 3A5-SX-11 (Xanthi nn line) were chosen for further analysis. The accumulation of MPΔ3–5 segregated in progeny of 3A5-SX-11 with a 3:1 ratio [(MPΔ3–5(+):MPΔ3–5(−)], suggesting that the MPΔ3–5 gene is expressed from a single locus in this plant line. The segregation ratio in seedlings from line 3A5-NN-7B was 59:1, suggesting that the MPΔ3–5 gene is expressed from three loci.

To test if the MPΔ3–5 protein was capable of supporting the spread of virus, plants that accumulated the MPΔ3–5 were inoculated with transcripts of a cDNA clone of TMV that does not express the MP due to a frame-shift mutation in the MP gene. The cDNA clone is described by Holt and Beachy, 1991, supra. As expected, these plants did not complement the spread of the movement-deficient TMV mutant and no disease symptoms were produced.

TABLE 2

Analysis of MPΔ3-5 transgenic plant lines

(a) Xanthi nn plants

| | Number of plants (out of five) | |
|---|---|---|
| Plant line | Accumulating MPΔ3-5 | Showing resistance |
| 3A5-SX-2 | 4 | 4 |
| 3A5-SX-3 | 5 | 4 |
| 3A5 -SX-4 | 5 | 5 |
| 3A5-SX-5 | 0 | 0 |
| 3A5-SX-8 | 5 | 5 |
| 3A5-SX-10 | 3 | 2 |
| 3A5-SX-11 | 5 | 4 |
| A5-SX-12 | 5 | 5 |
| 3A6-SX-1 | 4 | 4 |
| 3A6-SX-5 | 4 | 3 |
| 3A6-SX-6 | 2 | 2 |
| 3A6-SX-7 | 5 | 5 |
| 3A7-SX-2 | 4 | 4 |
| 3A7-SX-4 | 4 | 4 |
| 3A7-SX-5 | 4 | 4 |
| 3A7-SX-6 | 2 | 2 |
| 3A7-SX-7 | 1 | 0 |
| 3A7-SX-8 | 0 | 0 |
| 3A7-SX-9 | 3 | 3 |
| 3A7-SX-9A | 0 | 0 |
| Xanthi nn | / | 0 |

(b) Xanthi NN plants

| Plant line | No. of lesions | Percentage of control |
|---|---|---|
| 3A5-NN-2 | 17 (2) | 22.7 |
| 3A5-NN-4 | 39 (41) | 52 |
| 3A5-NN-7B | 19 (16) | 25.3 |
| 3A5-NN-10A | 56 (28) | 74.7 |
| 3A5-NN-10B | 12 (6) | 16 |
| 3A6-NN-2 | 7 (2) | 9.3 |
| 3A6-NN-9 | 24 (5) | 32 |
| 3A6-NN-10 | 54 (37) | 72 |
| 3A6-NN-11 | 41 (4) | 54.7 |
| 3A7-NN-1 | 35 (7) | 46.7 |
| 3A7-NN-4 | 17 (2) | 22.3 |
| 3A5-NN-2 | 85 (21) | 113.3 |
| Xanthi NN | 75 (37) | 100 |

(a) Five plants from each transgenic line were inoculated with TMV (0.5 μg/ml). The values given are the number of plants out of the five tested that accumulate the MPΔ3-5, and that show resistance. Accumulation was determined by slot-blot analysis of each plant as described in the examples. Plants that did not express systemic symptoms by 8 DPI were considered to be resistant. Control plants showed disease symptoms by 4–5 DPI.
(b) Ten plants from each transgenic Xanthi NN line were analyzed for resistance. The values given are the average number of necrotic local lesions per inoculated leaf counted 48–72 h after inoculation of plants with TMV (1.0 μg/ml). Values in parentheses represent the standard error. Percentage of control was calculated as the percentage of the number of lesions counted on the control Xanthi NN plants.

c) Determination of the Subcellular Accumulation of Dysfunctional Movement Protein The accumulation of the MPΔ3–5 gene product expressed in transgenic plant tissue was analyzed following subcellular fractionation and Western immunoblot analysis of proteins in each fraction and compared with similar studies using plant line 277, a transgenic plant previously shown to accumulate wild-type MP, (Deom et al., 1990, supra).

Subcellular fractionation was done as described by Deom, et al., 1990, supra. As shown in Table 3, approximately 90% of the WT MP co-purifies with an insoluble cellular component that largely contains cell walls (CW), the remaining 10% is in the membrane-rich fraction (P30) or in the soluble supernatant (S30). In contrast, the MPΔ3–5 protein was essentially evenly distributed between the cell wall and P30 fractions.

TABLE 3

Relative levels of wild-type MP and MPΔ3-5 in subcellular fractions from leaf tissue

| | Relative levels of MPΔ3-5, c.p.m. × $10^{-3}$ g $FW^{-1}$ | | |
|---|---|---|---|
| Plant line | CW | P30 | S30 |
| 277[a] | 1635 (91.4) | 147 (8.2) | 5 (0.3) |
| 3A5-SX-11 | 83 (41.8) | 103 (52) | 12 (6.2) |
| 3A5-NN-7B | 75 (38.3) | 113 (57.8) | 7 (3.9) |

The values are given in c.p.m. × $10^{-3}$ of $^{125}$I-labeled secondary antibody bound to immunoblots and represent the relative amounts of MPΔ3-5 or MP per gram fresh weight (FW) of leaf tissue. Leaves from three plants of each genotype were pooled for analysis. Values in parentheses represent the percentage of the total MP that is represented in the subcellular fraction. Proteins were extracted from fractionated leaf tissue, separated on a 12.5% polyacrylamide gel, transferred to nitrocellulose and reacted with anti-MP antibodies followed by $^{125}$I-labeled secondary antibody, as described in the examples. C.P.M. were determined after excising and counting each sample in a τ counter. CW, cell-wall-enriched fraction (20 μg protein analyzed per lane); P30, membrane-rich fraction (100 μg protein analyzed per lane); S30, soluble fraction (200 μg protein analyzed per lane).
[a]Plant line 277 expresses a wild-type TMV MP.

To compare the amounts of NP and MPΔ3–5 that accumulated in transgenic plants, total cellular proteins were extracted from leaf tissue by grinding two 5.9 mm diameter leaf disks per 50 μl grinding buffer (35 Mm potassium phosphate, pH 7.5, 10 Mm β-mercaptoethanol, 400 Mm NACl) and the insoluble material was discarded by centrifugation for 10 min in a microfuge. Samples of leaves from three plants of each genotype were pooled for analysis. The proteins were separated on a 12.5% polyacrylamide gel (50 ug protein per lane), transferred to nitrocellulose and reacted with anti-MP antibodies followed by $^{125}$I secondary antibody. The anti-MP antibodies were prepared as described in Deom, et al., 1987, supra, and the $^{125}$I-labeled donkey anti-rabbit serum was purchased from Amersham. The bands corresponding to MP and MPΔ3–5 were excised from the membrane and quantitated in a τ counter; c.p.m. are given below each lane. In addition to the transgenic plant line describe above, plant line 2005 is a Xanthi NN line that expresses the WT MP gene described in Deom et al., 1987, supra; 3A5-NN-7B and 3A5-SX-11 are transgenic plant lines which express the MPΔ3–5; 3A7-SX-8 is a transgenic line that does not express the MPΔ3–5 gene. As shown in FIG. 2, in the two transgenic plant lines tested, MPΔ3–5 accumulated to between 25 and 40% of the level of accumulation of WT MP in transgenic lines 277 and 2005.

d) Differences Between Transgenically Expressed WT-MP and Dysfunctional Movement Protein with Respect to Moleculer Size Exclusion Limits (SEL) of the Plasmodesmata for Sized Fluorescently Labeled Dextrans For microinjection studies, plants were grown in a controlled environment growth chamber for 3 to 4 weeks post-transplantation before being used. The temperature regime in the growth chamber was 24° C./18° C. (day/night) with a 16 h photoperiod at a PAR level of 230–280 μmol $M^{-2}$ $sec^{-2}$.

The plasmodesmal SEL in various tobacco lines was determined by monitoring intercellular coupling of microinjected fluorescent probes. The probes used were lucifer yellow CH (LYCH) with a molecular mass of 457 Da and fluorescein isothiocyanate-conjugated dextrans (F-dextrans) with molecular masses ranging from 3 to 10 kDa. These probes are describe in detail by Wolf S., et al., 1989, supra. All probes were dissolved in 5 Mm $KHCO_3$ and stored at 4°

C. The experimental system and procedures used for microinjection have been previously described in Ding et al., 1992, supra. Dye movement was monitored using an epifluorescence microscope (Leitz Orthoplan, Ernst Leitz GMBH, Wetzler, Germany) equipped with a blue (BP 390–490) excitation filter, a chlorophyll cutoff filter, and a video-intensified microscopy system (model C1966-20, Hamamatsu Photonics K.K., Hamamatsu City, Japan).

As shown in Table 4, in MP(+) plants the 10 kDa F-dextran readily moved out of injected cells into neighboring cells. However, in MPΔ3–5(+) plants, while the 3 kDa F-dextran moved from cell to cell, the 10 kDa F-dextrans failed to move. In MPΔ3–5(−) transgenic plants, neither the 3 kDa nor the 10 kDa F-dextran moved out of the injected cell. However, lucifer yellow CH (LYCH), with a molecular mass of 457 Da, moved freely from cell to cell in all the plant lines, regardless of MP gene expression (Table 4).

TABLE 4

Mobility of fluorescent probes between leaf mesophyll cells of various tobacco lines

| Plant line[a] | Leaf age[b] | LYCH | F-dextran 3 kDa | F-dextran 10 kDa |
|---|---|---|---|---|
| 277 | 6th | — | — | 5 (5) |
| 3A5-SX-11 | 5–7th | 5 (5) | 4 (5) | 0 (5) |
| 3A7-SX-8 | 5–6th | 5 (5) | 0 (5) | 0 (5) |
| WT | 10th | 5 (5) | 0 (5) | 0 (5) |

The data are presented as number of experiments manifesting cell-to-cell dye movement versus total number of experiments (in Parentheses). In each experiment two leaves from each plant were injected at two to three injection sites per leaf as a minimum. The different experiments were performed at different dates with different plants.
[a]277 expressed the wild-type MP of TMV; 3A5-SX-11 expresses MPΔ3–5; 3A7-SX-8 was transformed with, but did not express, the MPΔ3–5 gene; WT was non-transgenic Xanthi nn tobacco plants.
[b]The first leaf was defined as the youngest to attain a length of 5 cm.

e) Analysis of the Spread of Virus in Transgenic Plants that Accumulate Dysfunctional Viral Movement Protein For these studies, TMV (tobacco mosaic virus, U1 strain) and TMGMV (tobacco mild green mosaic virus, also referred to as TMV U2 strain) were propagated on Xanthi nn tobacco plants. Sunnhemp mosaic virus was grown in *Phaseolus vulgaris*. Virus was purified, and viral RNA was prepared according to Bruening, G., et al. *Virology*, 71: 498–571, 1976.

To determine to what extent accumulation of MPΔ3–5 had an effect on viral infection and spread, seedlings from transgenic plant line 3A5-SX-11 were inoculated with TMV (0.25 μg ml$^{-1}$) and analyzed for development of systemic symptoms in the upper leaves (FIG. 3). By the fifth day post-inoculation (DPI) plants that did not accumulate the MPΔ3–5 showed clear systemic symptoms of infection (FIG. 3a). By 7 DPI all or nearly all of the control plants displayed pronounced systemic symptoms (FIG. 3a). In contrast, by 9 DPI no systemic symptoms were produced on the MPΔ3–5(+) plants (FIG. 3a). At 10 DPI 10% of the MPΔ3–5(+) plants exhibited symptoms, and by 13 DPI half of the MPΔ3–5(+) plants showed systemic symptoms (FIG. 3a). When the TMV inoculum was raised fourfold (to 1.0 μg ml$^{-1}$), the MPΔ3–5(+) plants developed systemic symptoms by 9 DPI, and by 13 DPI nearly all of the MPΔ3–5(+) plants exhibited symptoms due to TMV infection (FIG. 3b). However, the symptoms that eventually developed on MPΔ3–5(+) plants upon TMV infection were less severe than those produced by the control plants. Inoculating the plants with TMV-RNA resulted in essentially the same results, i.e. a pronounced delay of systemic symptom development on MPΔ3–5(+) plants compared with control plants (FIG. 3*c*). MPΔ3–5(+) plants inoculated with a related tobamovirus, tobacco mild green mosaic virus (TMGMV) also showed a delay of systemic symptom development (FIG. 3*d*).

To quantify virus accumulation in the upper systemically infected leaves, the relative amount of TMV coat protein (CP) was measured at different times after inoculation in leaf samples taken from the third leaf above the inoculated leaf (Table 5). While TMV was detected in the upper leaves of control plants at 5 DPI, no virus was detected in MPΔ3–5(+) plants at that day. At 9 DPI TMV accumulation was detected in the MPΔ3–5(+) plants. However, the amount of virus detected in MPΔ3–5(+) plants was threefold lower than that in control plants (Table 5).

TABLE 5

Relative accumulation of TMV in systemic leaves of infected plants

| Line | Relative levels of CP (c.p.m. 10 μg $protein^{-1}$) 5 DPI | 9 DPI |
|---|---|---|
| 3A5+ | 0 | 471 (320) |
| 3A5− | 106 (48) | 1388 (155) |
| WT | 226 (19) | 1399 (225) |

Xanthi nn plants were inoculated with TMV (1.0 μg/ml). The values given are c.p.m. of $^{125}$I-labeled secondary antibody bound to immunoblots and represent the relative amount of TMP CP per 10 μg of protein extracted from fresh leaf tissue as described in Experimental procedures. Each value represents the average of 10 different samples. Values in parentheses represent the standard error.
3A5+, transgenic plants expressing MPΔ3-5 (line 3A5-SX-11);
3A5−, non-expressing transgenic plants (segregants of line 3A5-SX-11);
WT, wild-type Xanthi nn plants.

f) How to Determine that Resistance by Transgenic Plants Expressing Dysfunctional Viral Movement Protein is Due to the Reduction of Virus Spread and not Reduction of Virus Infection or Replication To confirm that MPΔ3–5 reduced virus spread per se rather than virus infection or replication the following experiment was performed. A TMV-based CDNA clone containing the gene encoding the reporter enzyme β-glucuronidase (GUS) (Jefferson et al., *Proc Natl Acad Sci USA,* 88: 2702–2706, 1986) in place of the MP gene was used to determine if, upon inoculation with TMV, MPΔ3–5 (+) plants produced the same number of initial infection sites as non-transgenic plants.

Leaf disks (32 mm in diameter) taken from inoculated leaves were immersed in 1 ml GUS assay buffer (50 mM Na-phosphate buffer, pH 7.0, 1 0 mM EDTA, 0.1% Triton X-100, 0.1% sucrose, 0.5 mM potassium ferrocyanide/ferricyanide, 10 mM β-mercaptoethanol) containing 0.5 mg $ml^{-1}$ X-Gluc. The samples were vacuum infiltrated, and incubated overnight at 37° C. The number of blue cells or areas were determined by microscopic examination.

The modified TMV containing the GUS gene (TMVΔM-GUS) was constructed by deleting most of the MP gene sequence (nt 4923–5402) from the viral cDNA clone and there inserting the GUS coding sequence. Upon inoculation of tobacco plants with an in vitro transcript of TMVΔM-GUS, the transcript retains the ability to replicate and produce virions, and in addition causes accumulation of the GUS enzyme. The accumulation of GUS activity necessarily reflects virus replication and the production of subgenomic RNAs, since translation of internal cistrons of TMV is known not to occur (Beachy and Zaitlin, *Virology,* 81:

160–169, 1977). However, TMVΔM-GUS does not move from cell to cell since it lacks most of the viral MP gene sequence. Cells in which the enzyme accumulates produce a blue stain following incubation with the GUS substrate X-Gluc. When transcripts of TMVΔM-GUS were inoculated to MP(+) plants, infection and the accumulation of GUS spread from cell to cell as expected due to complementation by the transgene. In contrast, when MPΔ3–5(+) plants or non-transgenic plants were inoculated with TMVΔM-GUS only single cells showed GUS activity, indicating initial sites of viral replication of blue cells were found on leaves of MPΔ3–5(+) and non-transgenic plants inoculated with TMVΔM-GUS. This suggests that resistance in MPΔ3–5(+) plants was not due to inhibition of replication per se.

g) Analysis of Resistance to Viral Spread in Transgenic Local Lesion Hosts

A transgenic local lesion host which accumulates MPΔ3–5, plant line 3A5-NN-7B, was also tested by inoculating $R_1$ seedlings with TMV, TMV-RNA, TMGMV and with a distantly related tobamovirus, SHMV. In all cases, MPΔ3–5(+) plants developed 1/4 to 1/7 the number of necrotic local lesions compared with the control non-transgenic plants (Table 5). Despite the low amino acid sequence homology between the SHMV MP and the TMV MP (less than 30%), the number of lesions caused by SHMV was reduced as a result of the expression of MPΔ3–5. Moreover, the lesions that developed on MPΔ3–5(+) plants were significantly smaller in diameter (by about 50%) than the lesions that developed on the control plants (FIG. 4). Two of the $R_1$ seedling progeny of the 3A5-NN-7B plant line that did not accumulate MPΔ3–5 developed the same number of lesions, and the lesions were of the same size, as those that developed on control plants.

In all experiments there was a clear correlation between accumulation of the MPΔ3–5 protein and symptom inhibition, i.e. numbers and size of necrotic local lesions or a delay in systemic symptom development.

TABLE 6

Effect Of MPΔ3-5 on number of necrotic local lesion

| Innoculum | Percentage AA[b] identity | conc. ($\mu$g ml$^{-1}$) | Plant line 3A5-NN-7B | Plant line Xanthi NN | % of control |
|---|---|---|---|---|---|
| TMV | 100 | 0.25 | 10 (7) | 74 (40) | 13.5 |
| TMV | 100 | 1.0 | 51 (42) | 190 (54) | 26.8 |
| TMV-RNA | 100 | 1.3 | 36 (21) | 77 (30) | 46.7 |
| TMGMV | 57 | 2.0 | 8 (7) | 40 (19) | 20 |
| SHMV[a] | 29 | 10.0 | 69 (24) | 165 (49) | 41.8 |

The values given are number of necrotic local lesions per inoculated leaf counted 48-96 HPI of plants with virus or viral RNA. Each sample was inoculated to 15 leaves.
Values in parentheses represent the standard error.
Conc. , concentration;
AA, amino acids.
[a]Lesions induced by SHMV were counted 8 DPI.
[b]The amino acids sequence comparison was done by allowing small gaps.

Example 2

Determination of Multi-Virus Resistance in Transgenic Tobacco Plants that Express Dysfunctional Viral Movement Protein This example demonstrates that tobacco plants expressing the TMV dysfunctional protein, MPΔ3–5, have the ability to restricted viral movement and delay of disease symptoms when inoculated with other related virus of the tobamovirus group as well as viruses from other groups/families. Plants expressing MPΔ3–5 retard disease symptom development and reduce the accumulation of additional tobamoviruses and two viruses from the MP family one, tobacco rattle tobravirus (TRV) and peanut chlorotic streak caulimovirus (PClSV), and a member from the MP family two, alfalfa mosaic ilarvirus (AlMV).

a) Plants

Transgenic *Nicotiana tabacum* cv. Xanthi nn lines 274 and 277 and *N. tabacum* cv. Xanthi NN line 2005 that express a gene encoding the TNV MP (MP+) were described by Deom, C. M., et al., 1987, supra. Transgenic *N. tabacum* cv. Xanthi NN line 3A5-SX-11 and *N. tabacum* cv. Xanthi nn lines 3A5-NN-7B and 3A6-NN-2 expressing the gene encoding a MPΔ3–5 are described above. *Nicotiana tabacum* cv. Xanthi nn line 3A7-SX-8, a transgenic plant line that does not express the MP or MPΔ3–5 genes (MP–), and nontransformed *N. tabacum* cv. Xanthi NN were used as negative controls. All plants were grown in a greenhouse (University of California, Riverside) or in controlled environmental chambers as described in Example 1.

b) Virus Propagation and Inoculation

Using methods commonly practiced in the art, tobamovirus TMV strain U1, tobamovirus Ob, which systemically infects *N. tabacum* Xanthi NN (Padgett, H. S. & Beachy, R. N., *The Plant Cell* 5, 577–586, 1993), Cg, a cruciferous tobamovirus (kindly provided by M. Ishikawa and T. Ohno, Hokkaido University, Japan), tomato mosaic tobamovirus (ToMV), tobacco rattle tobravirus (kindly provided by D. J. Robinson, S.C.R.I., Invergowrie, Scotland), and alfalfa mosaic ilarvirus were maintained in appropriate Nicotiana spp. Peanut chlorotic streak caulimovirus, generously provided by R. Richins, University of California, Riverside) was maintained in *N. tabacum* in a growth chamber at 32° C. Viruses were identified by inoculation to diagnostic host plants and by reactions to virus specific antibodies. Source plant leaves were triturated, and extracts were diluted in inoculation buffer (20 mM phosphate buffer, pH 7.0, 1 mM EDTA). Inoculum was applied to a single carborundum-dusted leaf on each of eight plants of lines 274, 277, 3A5-SX-11 and 3A7-SX-8 or 2005, 3A5-NN-7B, 3A6-NN-2 and NN plants. Extracts were also inoculated onto *Chenopodium amaranticolor* to quantitate the infectivity of each inoculum. The average number of lesions on *C. amaranticolor* represented a relative inoculum potential (IP) for each of the viruses tested. Only those plants inoculated with PCLSV were grown in a growth chamber at 32° C.

c) Symptom Development Each leaf of each plant, including the inoculated leaf, was observed for disease symptom appearance. The maximum score was 5, indicating that the plant had at least 5 leaves with disease symptoms; a score of zero identified a plant devoid of symptoms. A score of 1 reflected the appearance of symptoms on inoculated leaves. The intensity of symptoms was not scored. The average number of tobacco leaves that developed visible symptoms on a plant was plotted against time (days after inoculation or DAI). Analysis of variance of symptoms on the transgenic plants was compared to symptoms on negative controls. Differences at the 95% level using the Fischer PLSD test were considered to be significant.

d) Quantitation of Virus

On the first day that systemic symptoms appeared on the control plants inoculated with TMV, PClSV or AlMV, a 1 cm diameter disc was taken from the uppermost leaf (>5 cm in length) on all plants and discs from each treatment were pooled. The same leaf was sampled in subsequent days. The pooled samples were triturated in 35 mM $KH_2PO_4$ pH 7.5, 10 mM 2-mercaptoethanol, 400 mM NaCl, and the total soluble protein in the extracts was determined using bicinchoninic acid protein assay reagent (Pierce, Rockford, Ill.). An equivalent amount of protein and different amounts of the appropriate purified virus were separated by SDS-PAGE (Laemmli, U.K. *Nature* (London) 277, 680–685, 1977) in 12.5% gels and transferred to nitrocellulose (Towbin, H., et al, *Proc Natl Acad Sci USA* 76, 4350–4354, 1979). The membrane was treated with the appropriate viral coat protein rabbit antibody, followed by an alkaline phosphatase conjugated antirabbit antibody and developed with the ProtoBlot® II AP System purchased from Promega Corp., supra. The amount of coat protein detected on a Sci-Scan 5000 densitometer (United States Biochemical) was interpolated from a standard curve. TRV was quantitated by the following biological assay. The uppermost >5 cm leaf was sampled from plant inoculated with TRV after symptoms appeared on the control plants. Each sample was ground in inoculation buffer to a standard dilution and inoculum was applied to leaves of *C. amaranticolor*. The leaves were observed several days later for the presence or absence of TRV-induced lesions.

e) Plants Challenged with Tobamoviruses

Figure 5:
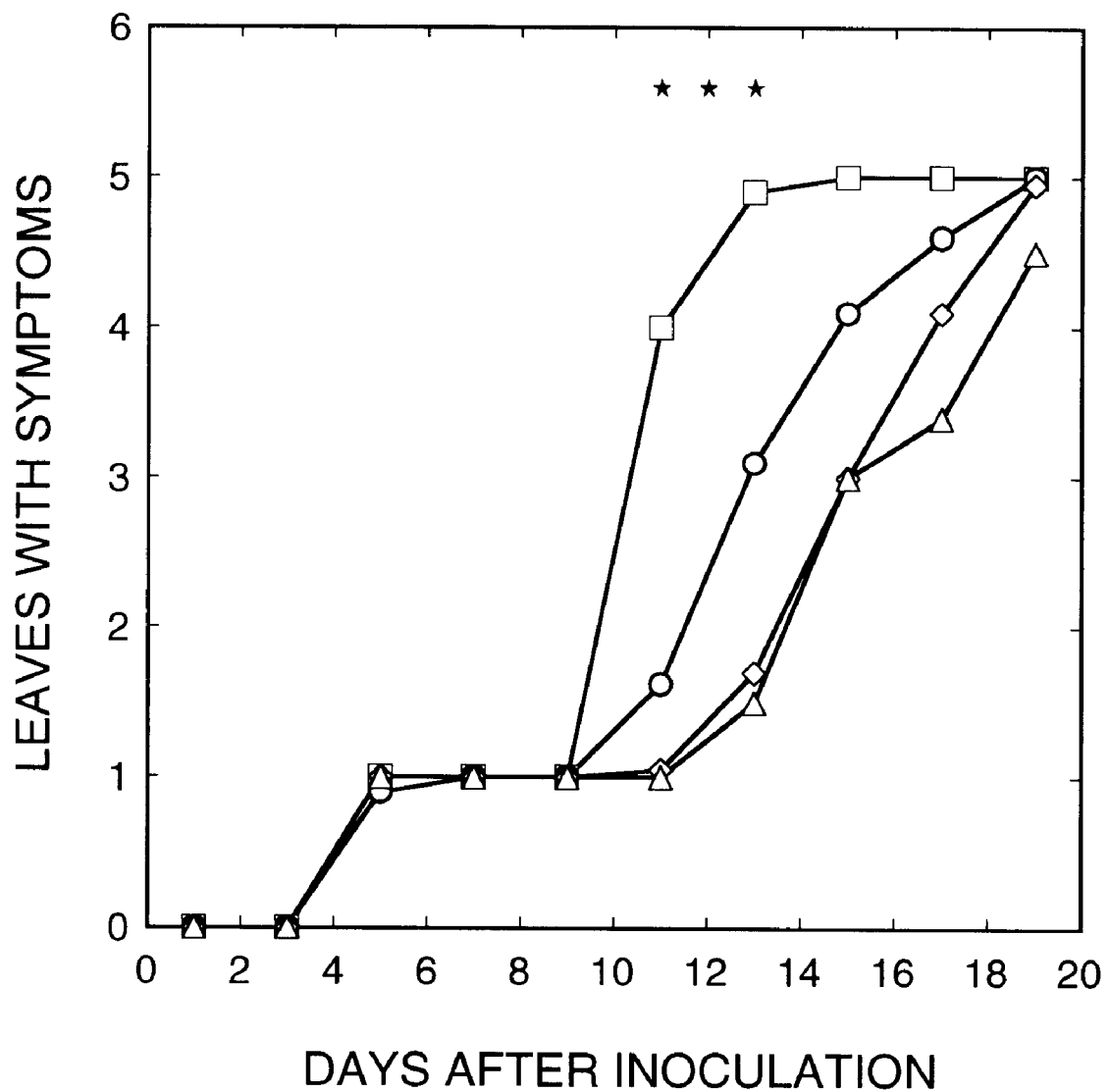

As shown in Example 1, plant lines that accumulate MPΔ3–5 restricted the spread of TMV and two other tobamoviruses. To determine whether there was similar resistance to these and other tobamoviruses under greenhouse conditions eight plants of lines 3A7-SX-8 (MP−), 274 (MP+), and 3A5-SX-11 (MPΔ3–5+), all having the genotype nn, were inoculated with TMV and monitored for systemic disease symptoms over a 10 day period. The TMV inoculum produced an average of 50 lesions per leaf on *C. amaranticolor* and corresponded with the IP (inoculum potential) shown in Example 1 achieved with 0.25 ug/ml of TMV. Under greenhouse conditions symptoms were delayed by 3–4 days on the 3A5-SX-11 line that accumulated the TMV MPΔ3–5 (Table 7). Immunoblot assays revealed that less virus accumulated in the leaves above the inoculated leaves of plant line 3A5-SX-11 than in either plant line 274 (which accumulates a functional MP) or plant lines that do not accumulate a MP or a MPΔ3–5 (plant line 3A7-SX-8). This data was similar to that in Example 1. Plant lines 3A5-NN-7B (MPΔ3–5+) and 3A6-NN-2 (MPΔ3–5+) delayed systemic symptom development of tobamovirus Ob by 3 days as compared to negative controls (Table 7 and FIG. 5), while plants expressing a functional MP (2005) exacerbated symptom development of Ob. Inoculation of tobamovirus Cg to plant line 3A5-NN-7B (MPΔ3–5+) reduced the numbers of local lesions by 78% at low IP and 56% at high IP (Table 7). Plant line 3A5-SX-11 expressing the MPΔ3–5 delayed systemic symptom development of ToMV by 3 days compared with control plants (Table 7).

TABLE 7

Resistance in tobacco plants to tobamoviruses due to the DMP.

| VIRUS | µg/ml | PLANT LINE | SYMPTOM* |
|---|---|---|---|
| TMV-U1 | 0.25 | 3A5-SX-11 | 3 day delay of SS |
|  | 0.25 | 3A5-SX-11 | 14 day delay of SS† |
|  | 0.50 | 3A5-NN-7B | 83% reduction in #LL |
|  | 0.50 | 3A5-NN-7B | 75% reduction in #LL† |
|  | 1.00 | 3A5-NN-7B | 85% reduction in #LL |
|  | 0.50 | 3A6-NN-2 | 85% reduction in #LL |
|  | 1.00 | 3A6-NN-2 | 91% reduction in #LL† |
| TMGMV | 2.00 | 3A5-SX-11 | 3 day delay of SS |
|  | 2.00 | 3A5-SX-11 | 14 day delay of SS† |
|  | 2.00 | 3A5-NN-7B | 80% reduction in #LL† |
| SHMV | 10.00 | 3A5-NN-7B | 58% reduction in #LL† |
| Ob | 0.25 | 3A5-NN-7B | 3 day delay of SS |
|  | 0.25 | 3A6-NN-2 | 3 day delay of SS |
| Cg | 1.00 | 3A5-NN-7B | 78% reduction in #LL |
|  | 2.00 | 3A5-NN-7B | 56% reduction in #LL |
| ToMV | 0.50 | 3A5-SX-11 | 3 day delay of SS |

*Data presented is relative to symptoms on the appropriate negative controls. Plant lines designated SX are systemic hosts for all of these tobamoviruses. Tobamovirus Ob does not cause necrotic local lesions on NN plant lines, but all others do.
SS = systemic symptoms;
LL = number of local lesions.
†Data from Lapodit, M., et al., The Plant Journal, 4:959–970, 1993, obtained under controlled artificial conditions. All other data obtained under greenhouse conditions.

f) Plants Challenged with TRV

Figure 6:
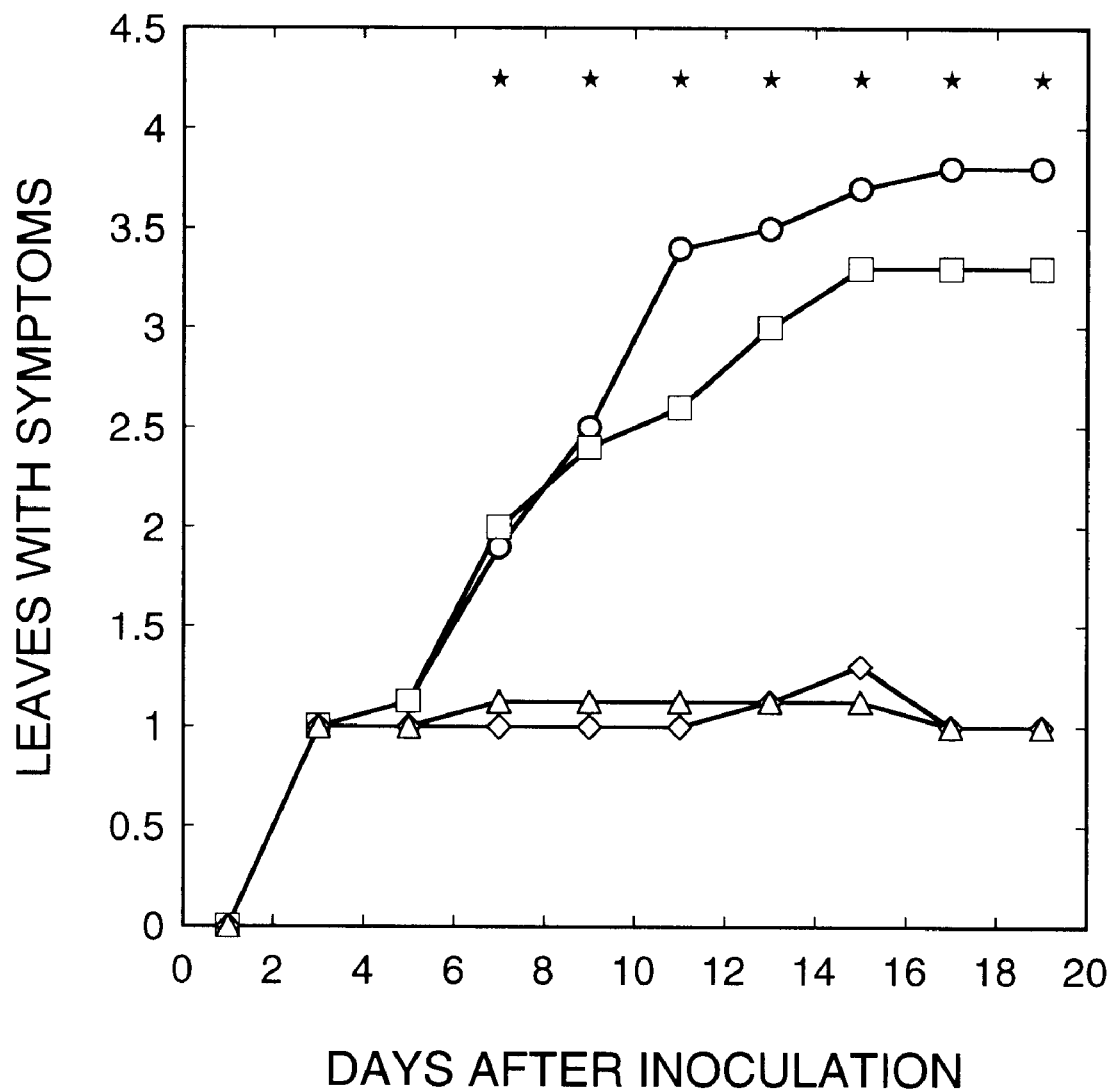

To assess resistance to TRV, virus was inoculated to Xanthi NN (MP−) and plant lines 2005 (MP+), 3A5-NN-7B (MPΔ3–5+) and 3A6-NN-2 (MPΔ3–5+). When plants were inoculated with an inoculum that produced an average of 260 lesions per leaf on *C. amaranticolor* the inoculated leaves of all tobacco lines produced characteristic local necrotic reactions of equal severity that appeared at the same time on each line. The control plant line (MP−) developed systemic symptoms by 7 DAI, but there were no systemic symptoms on plant lines 3A5-NN-7B (MPΔ3–5+) or 3A6-NN-2 (MPΔ3–5+) by 20 DAI (FIG. 6). In a second experiment in which the TRV IP was sufficient to cause an average of 38 lesions on *C. amaranticolor,* leaves above the inoculated leaf were sampled from tobacco plants at 11 DAI and extracts were inoculated to *C. amaranticolor.* Only extracts from the control plants induced large numbers of lesions indicative for TRV on *C. amaranticolor.* No virus was recovered from 8/8 of the 3A5-NN-7B plants or 5/8 of the 3A6-NN-2 plants. Virus was recovered from 3/8 of the 3A6-NN-2 plants but lesion numbers were low (Table 8).

TABLE 8

Systemic infection of plants inoculated with TRV.*

| PLANT LINE | # PLANTS SYSTEMICALLY INFECTED/TOTAL PLANTS |
|---|---|
| NN (MP−) | 8/8 † |
| 2005 (MP+) | 8/8 |

TABLE 8-continued

Systemic infection of plants inoculated with TRV.*

| PLANT LINE | # PLANTS SYSTEMICALLY INFECTED/TOTAL PLANTS |
|---|---|
| 3A5-NN-7B (MPΔ3-5) | 6/8 |
| 3A6-NN-2 (MPΔ3-5) | 3/8 ‡ |

*At 11 DAI, upper leaves from plants inoculated with TRV were homogenized in buffer and clarified extracts were inoculated to C. amaranticolor, which were subsequently scored for the presence of lesions.
†Two tobacco plants that showed TRV symptoms yielded negative bioassays
‡One of the tobacco plants that yielded a positive bioassay was negative for TRV symptoms until 20 DAI. The two other plants showed low virus accumulation.

g) Plants Challenged with PClSV

Plant lines 3A5-SX-11 (MPΔ3–5+), 274 (MP+), and 3A7-SX-8 (MP−) were inoculated with leaf extracts containing the caulimovirus Pclsv and the plants were grown in a growth chamber at 32° C. Immunoblot analysis of samples collected from the third, sixth and ninth leaves above the inoculated leaf at 30 DAI did not detect virus in the MPΔ3–5(+) plants (Table 9). There was between 3 and 6 times as much virus in plants expressing a functional MP as compared to non-transgenic plants, suggesting that the MP exacerbated the spread or accumulation of PClSV in these plants. Symptoms were difficult to evaluate because of the chlorosis caused by the elevated temperatures.

TABLE 9

Accumulation of Pclsv in upper tissues of transgenic plants.*

| PLANT LINE | LOCATION OF LEAF ABOVE INOCULATED LEAF | | |
|---|---|---|---|
| | +3 | +6 | +9 |
| 3A7-SX-8 (MP−) | 0 | 100 | 100 |
| 274 (MP+) | 180 | 330 | 570 |
| 3A5-SX-11 (MPΔ3-5) | 0 | 0 | 0 |

*Values are % of Pclsv extracted from the upper tissues of plants at DAI 30 per μg of tobacco plant protein as compared with virus in 3A7-SX-8. Virus was quantitated by immunoblot analysis.

h) Plants Challenged with AlMV

Figure 7A:
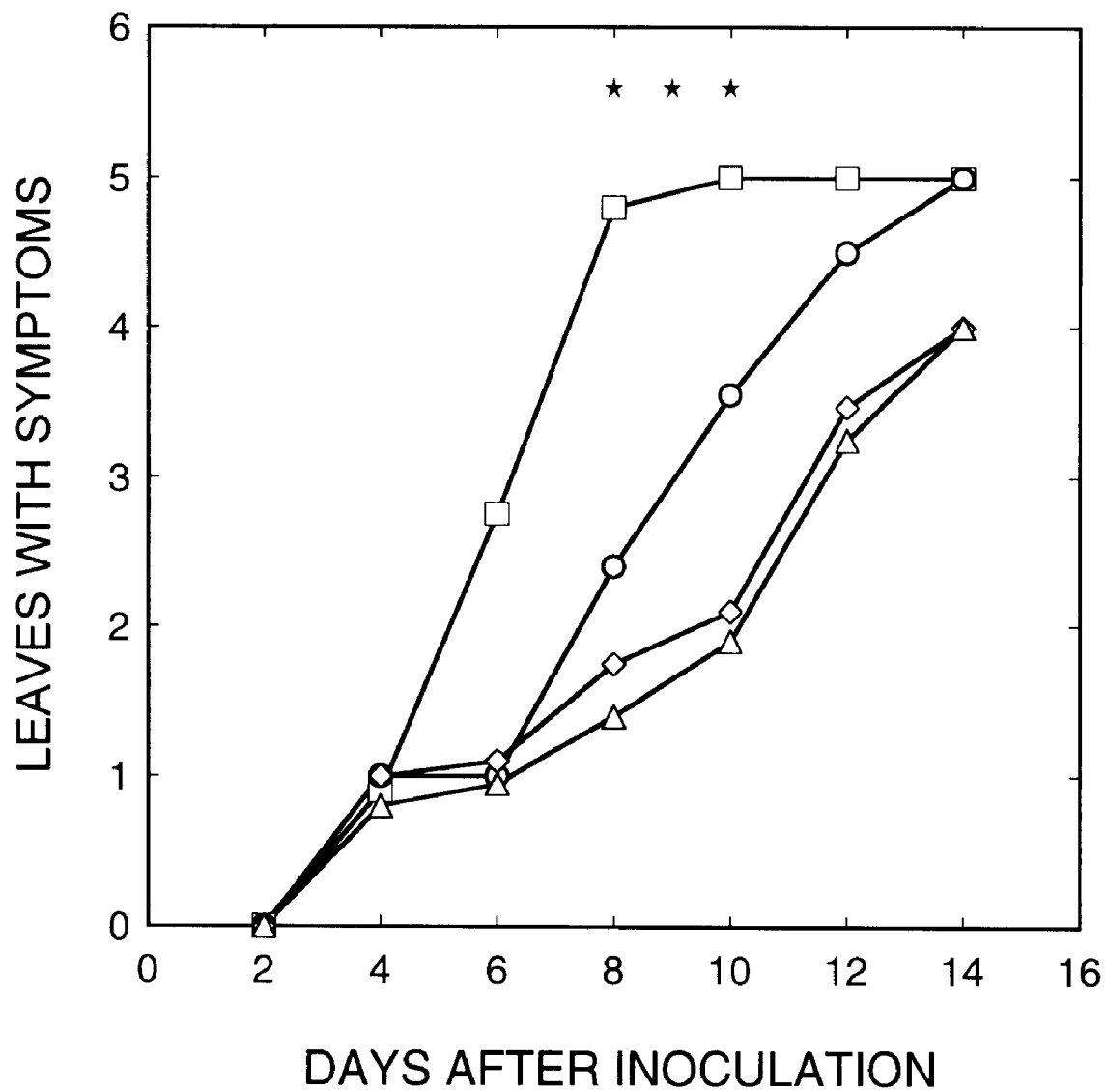
Figure 7B:
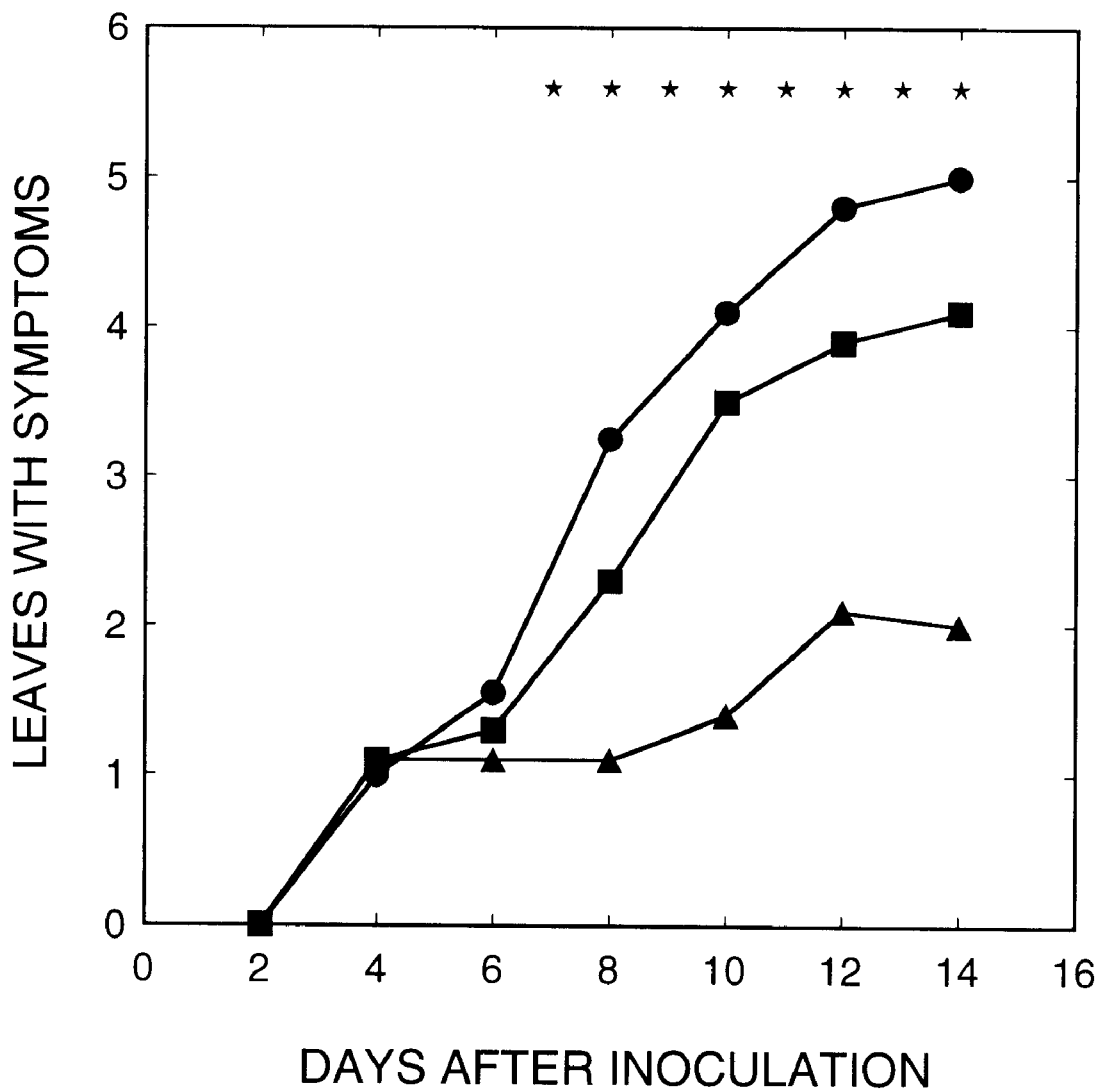

Studies with AlMV were performed on Xanthi nn and NN plant lines with inocula that produced high (>200) or low numbers of lesions on C. amaranticolor (Golemboski, D. B., et al., Proc Natl Acad Sci USA 87: 6311–6315, 1990). In all studies the inoculated leaves of all tobacco lines developed the same number and type of local necrotic reactions at the same time. At the high level of inoculum non-transgenic nn plants and plants with MP (line 274) developed systemic symptoms within 4–6 days. Plant line 3A5-SX-11 (MPΔ3–5+) developed symptoms 2 to 3 days later and eventually all plants developed symptoms. In a subsequent study both nn and NN plant lines were challenged with AlMV at a low level of inoculum. All plant lines with the MPΔ3–5 gene developed symptoms 5 to 10 days later than nontransgenic plants or plants with MP (FIGS. 7a and 7b). Immunoblot analysis of virus in extracts of leaves demonstrated that there was little or no detectable AlMV in the tissues above the inoculated leaves of the plant lines 3A6-NN-2 or 3A5-SX-11 that express MPΔ3–5 (Table 10); plant line 3A5-NN-7B delayed the accumulation of virus in this study. These studies demonstrated that the MPΔ3–5 had little effect on the infection of inoculated leaves, but the MPΔ3–5 did retard or block the spread of AlMV to upper leaves.

TABLE 10

Accumulation of AlMV in upper tissues of transgenic plants.*

| PLANT LINE | DAYS AFTER INOCULATION | | |
|---|---|---|---|
| | 7 | 8 | 9 |
| NN (MP−) | 37 | 46 | 56 |
| 2005 (MP+) | 125 | 159 | 77 |
| 3A5-NN-7B (MPΔ3-5) | 3 | 28 | 54 |
| 3A6-NN-2 (MPΔ3-5) | 0 | 0 | 0 |
| 3A7-SX-8 (MP−) | 34 | 70 | 53 |
| 274 (MP+) | 28 | 51 | 42 |
| 3A5-SX-11 (MPΔ3-5) | 0 | 0 | 0 |

Figure 3A:
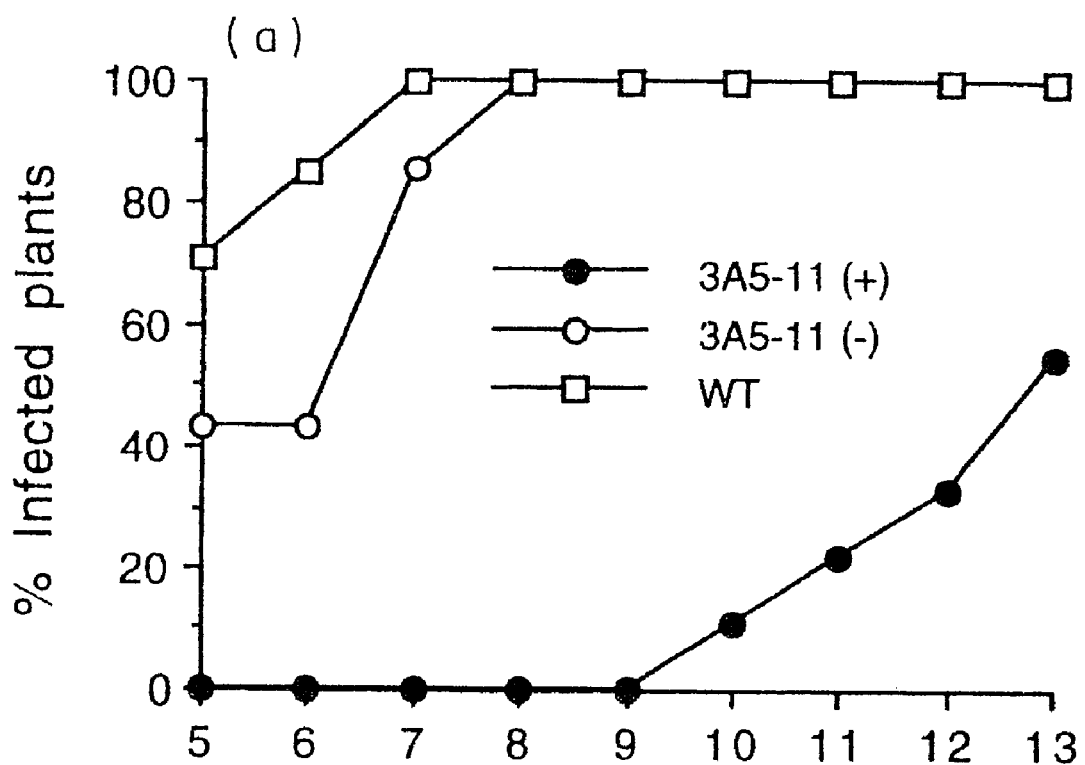
Figure 3B:
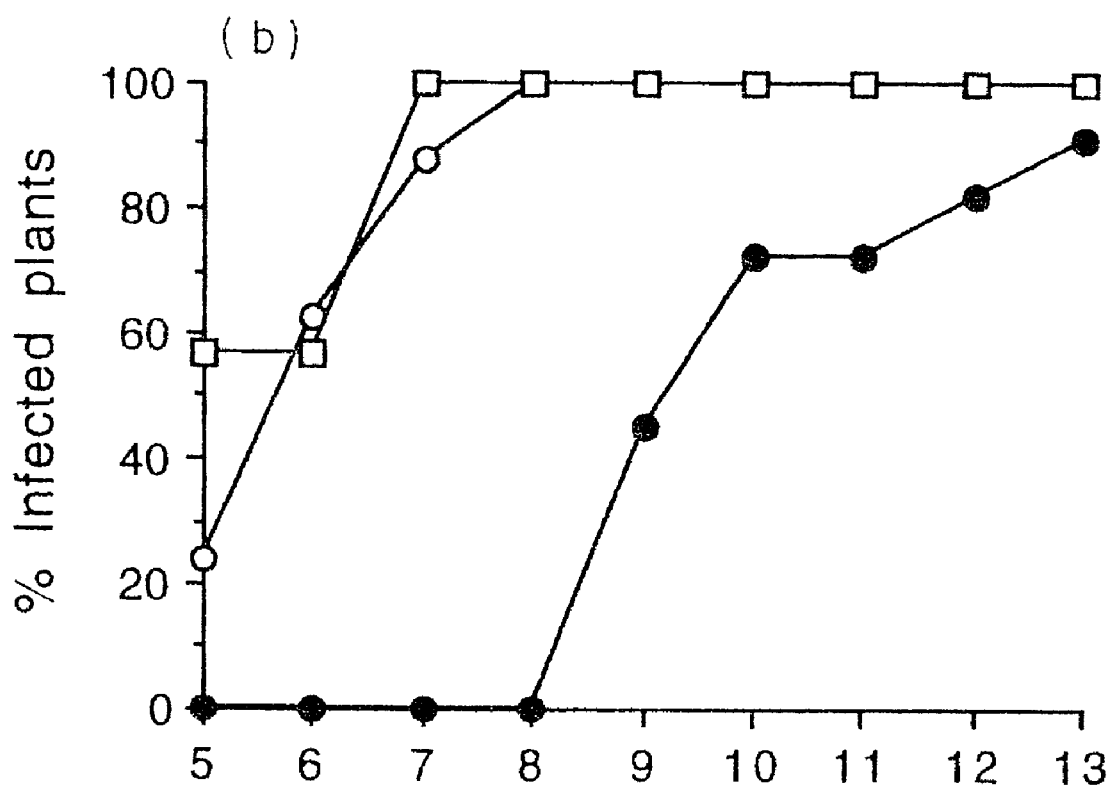
Figure 3C:
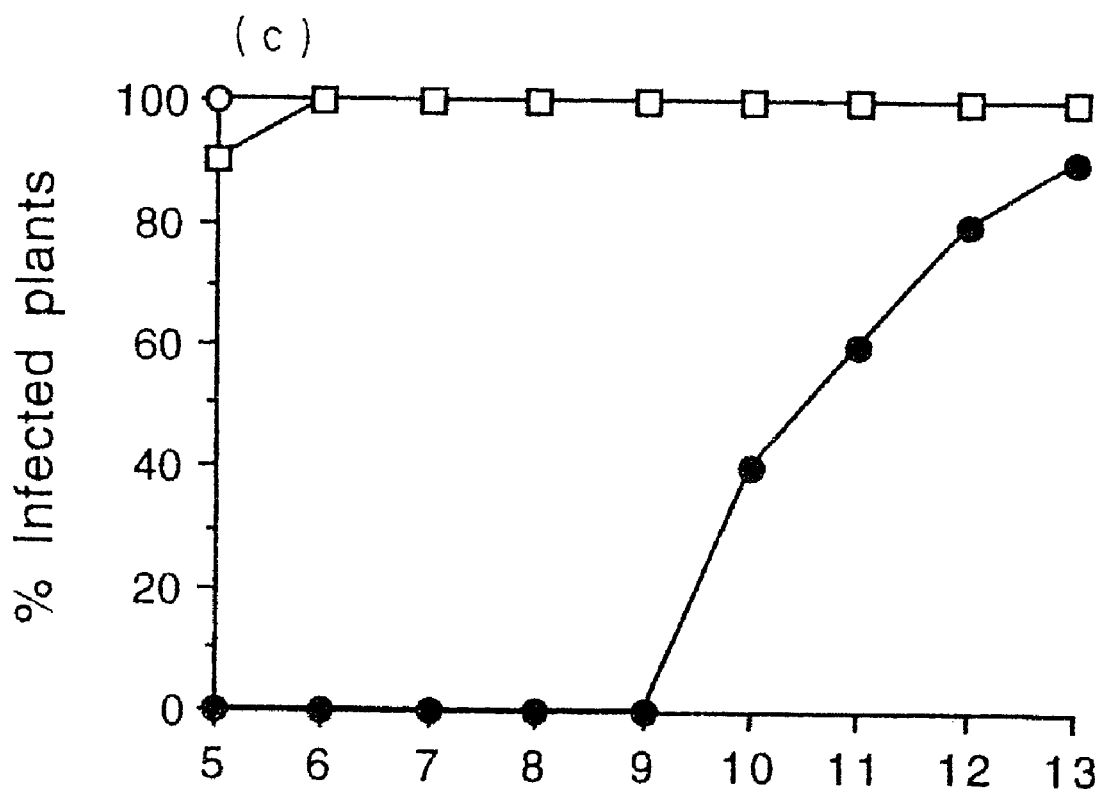
Figure 3D:
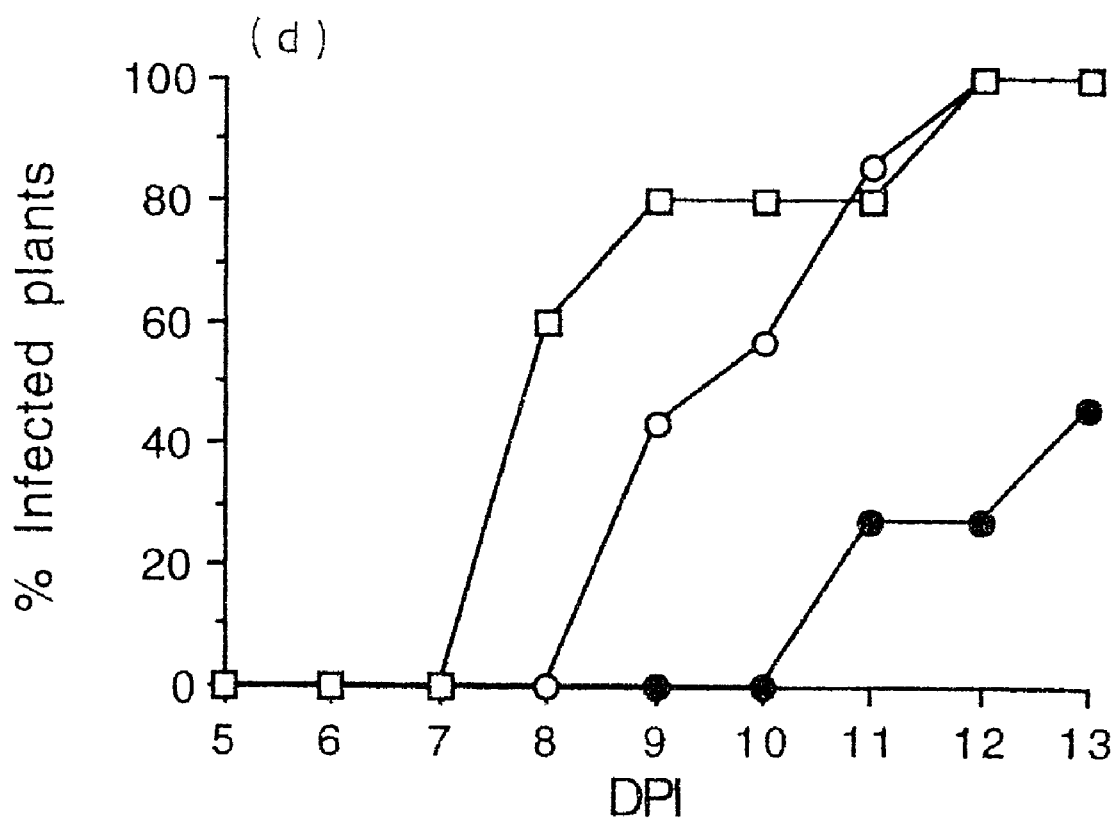
Figure 4A:
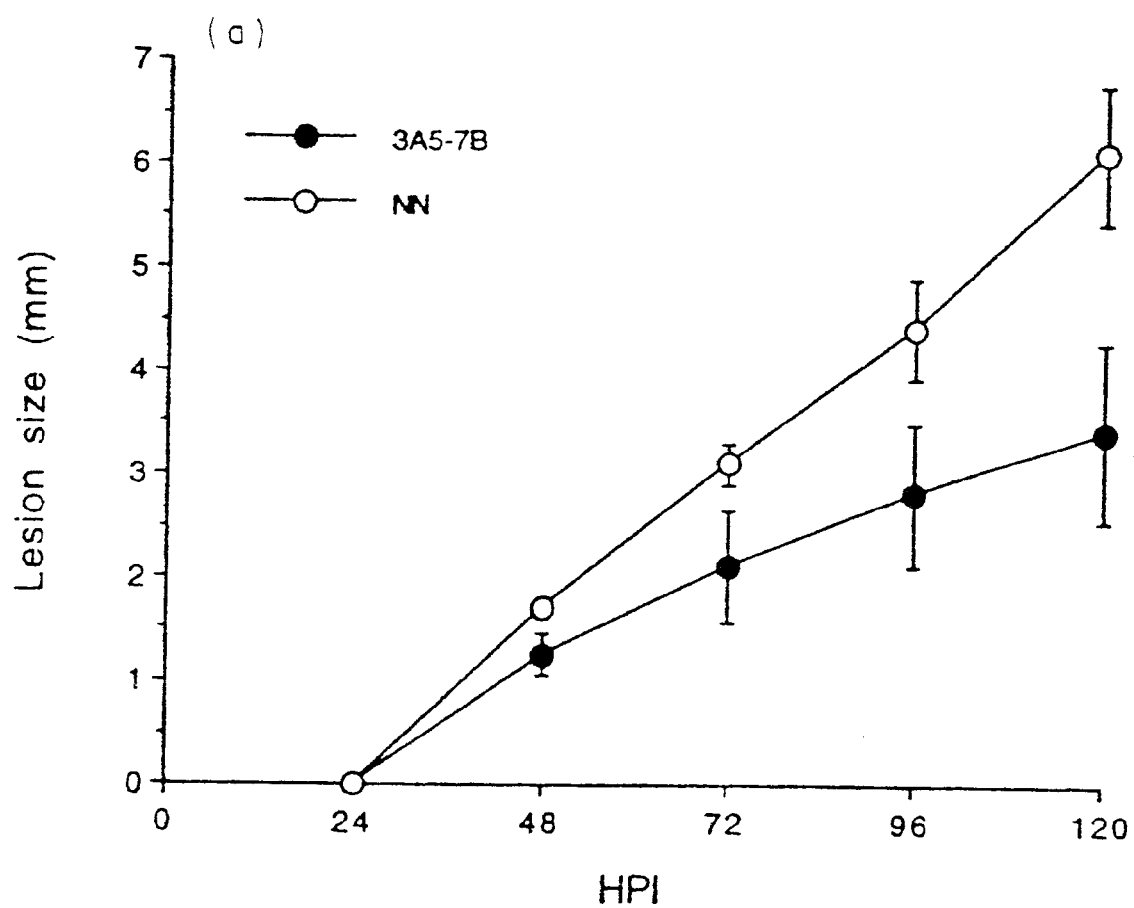
Figure 4B:
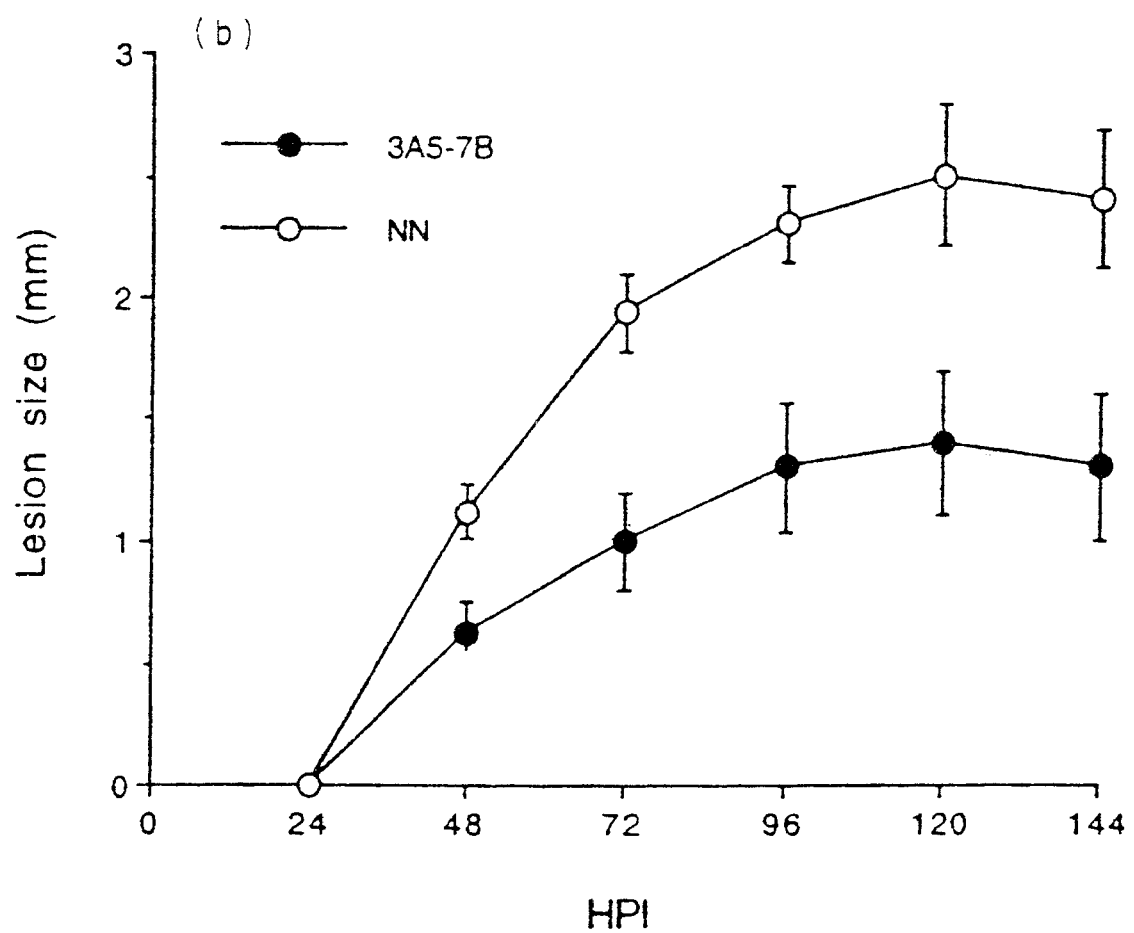

*Numbers are ng of AlMV extracted from the pooled samples of the upper tissues of plants from FIGS. 3a and 3b per μg of total plant protein as determined by immunoblot analysis.

Example 3

Transient Assays for the Identification of Mutant Viral Movement Proteins that Block Virus Spread Two types of transient assays can be utilized for the identification of transgenically expressed mutant viral movement proteins capable of interfering with the spread of virus infection. Both assays involve analysis for the development of disease symptoms that result after simultaneous expression of MP and the candidate mutated viral movement protein. In one assay symptoms are analyzed in plants that have been simultaneously inoculated with equal amounts of two infectious clones, one clone containing MP and the other containing the candidate mutated viral movement protein. In the second assay, symptoms are analyzed in plants inoculated with an infectious clone containing a cassette that causes the production of equal numbers of molecules of the two proteins, MP and candidate mutated viral movement protein. In both assays, if the mutated movement protein is capable of interfering with the wtmp and blocks the intercellular movement of virus, the spread of disease symptoms from the initial site of inoculation will be stopped or delayed.

a) Transient Assay Incorporating Separate Infectious Clones

This assay requires the preparation of an infectious clone of the virus of interest. To prepare the infectious clone one prepares a CDNA copy of the viral genome. To make the clone infectious, an appropriate transcriptional, e.g., T7 promoter, is inserted into the clone at a point that under the appropriate in vitro conditions there is synthesis of RNA that can cause infection when inoculated to an appropriate host. An alternative approach is to place the viral CDNA downstream of a transcriptional promoter that is active in plant cells causing virus infection when transfected into plant cells.

Two infectious clones are constructed; the first containing the MP and the second containing the mutant MP. Mutant and wild type infectious RNAs are coinoculated in ratios that lead to a high probability that most or all cells are co-infected by both. Co-infection is common amongst viruses that are co-inoculated but it should be noted that attempts to sequentially infect plants can be unsuccessful. If the mutant MP acts in a dominant manner and prevents the MP from functioning, the infection will be limited, and may either result in sites of infection that are restricted in size or the infection will be restricted of slowed in systemic spread.

b) Transient Assay Incorporating Expression Cassette that Produces Equal Amounts of MP and Mutant MP This assay relies upon a genetically engineered TMV that contains an expression cassette that causes the production of equal numbers of two proteins from a single promoter. The preparation of the cassette is described by Marcos and Beachy, *Plant Molecular Biology* 24: 495:503 1994. In brief, the cassette (PPRO1) includes the tobacco etch virus (TEV) nuclear inclusion (NIa) proteinase coding region flanked on each side by its corresponding heptapeptide cleavage sequence along with cloning sites for in frame insertion of two different open reading frames. The cassette allows the synthesis, under the control of a single transcriptional promoter, of two proteins in equimolar amounts as part of a polyprotein which is cleaved into individual mature products by the TEV protease.

In the current assay the cassette will be constructed to encode the wtMP along with the mutant movement protein. Using commonly practiced methods of genetic engineering, the gene cassette is introduced into the genome of TMV (or other viruses) in place of the gene encoding the wild type MP. Using the methods described in examples 1 and 2, tobacco plants are inoculated with this engineered TMV. For a control, wild type TMV is used as the inoculum. The plants are then analyzed for the development of disease symptoms. If the mutant MP interferes with the MP, infections will be confined to small foci and will either not spread locally or will do so at a slower rate when compared with the controls. When this occurs the mutant MP genes are candidates for use as virus resistant genes and can be further tested in transgenic tobacco plants.

It is apparent to those skilled in the art that a similiar strategy could also be taken to incorporate the polyprotein cleavage cassette into the cloned cDNA for viruses other than TMV.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of producing a viral resistant plant said method comprising the step of transforming the plant with a gene encoding a viral movement protein derived from tobacco mosaic virus, wherein said viral movement protein is mutated between amino acids 2 and 8 in the amino terminus, and wherein said protein is able to bind the plasma membrane and cell walls of the plant and inhibit the intercellular and/or systemic movement of a virus selected from the group consisting of Ilar viruses, bromovirus, caulimovirus, hordeivirus, luteovirus, tobamovirus and tospovirus.

2. The method of claim 1 wherein said inhibited virus is a Tobamovirus.

3. The method of claim 1 wherein the mutation is a deletion of amino acids 3–5.

4. The method of claim 1 wherein said inhibited virus is a Tobamovirus.

5. The method of claim 4 wherein the mutation is a deletion of amino acids 3–5.

* * * * *